US010881375B2

(12) United States Patent
Takimoto et al.

(10) Patent No.: US 10,881,375 B2
(45) Date of Patent: Jan. 5, 2021

(54) IMAGING DIAGNOSIS APPARATUS HAVING NEEDLING NAVIGATION CONTROL SYSTEM AND A NEEDLING NAVIGATION CONTROLLING METHOD

(71) Applicant: Toshiba Medical Systems Corporation, Otawara (JP)

(72) Inventors: Masao Takimoto, Tochigi-ken (JP); Fumiyasu Sakaguchi, Tochigi-ken (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

(21) Appl. No.: 15/398,242

(22) Filed: Jan. 4, 2017

(65) Prior Publication Data

US 2017/0112465 A1    Apr. 27, 2017

Related U.S. Application Data

(63) Continuation of application No. 12/275,886, filed on Nov. 21, 2008, now abandoned.

(30) Foreign Application Priority Data

Nov. 22, 2007    (JP) .................................. 2007-303040

(51) Int. Cl.
*A61B 8/00*    (2006.01)
*A61B 8/08*    (2006.01)
(Continued)

(52) U.S. Cl.
CPC .............. *A61B 8/0841* (2013.01); *A61B 6/12* (2013.01); *A61B 8/0833* (2013.01); *A61B 8/466* (2013.01);
(Continued)

(58) Field of Classification Search
CPC ........... A61B 8/483; A61B 34/20; A61B 6/12; A61B 8/0833; A61B 8/0841; A61B 8/466; A61B 8/5207
See application file for complete search history.

(56) References Cited

U.S. PATENT DOCUMENTS 5,080,104 A    1/1992    Marks et al.
5,963,211 A    10/1999    Oikawa et al.
(Continued)

FOREIGN PATENT DOCUMENTS

JP    4-227239    8/1992
JP    5-277091    10/1993
(Continued)

OTHER PUBLICATIONS

Office Action dated May 4, 2017 in co-pending U.S. Appl. No. 12/275,886.
(Continued)

*Primary Examiner* — Christopher L Cook
(74) *Attorney, Agent, or Firm* — Oblon, McClelland, Maier & Neustadt, L.L.P.

(57) ABSTRACT

An ultrasound imaging diagnosis apparatus and a method for supporting safe and exact puncturing into a target region in a patient's body are provided. In the apparatus, a regions setting unit sets a target tumor region for puncturing, blood vessel and organ regions that are located near the tumor region based on 3-D volume data. To avoid insertions into blood vessel and organ regions, a needle position detecting unit detects the tip position and inserting direction of the needle before and during insertion. An expected inserting position calculating unit calculates an expected inserting position and an insertion error region to the tumor region based on the tip position data, inserting direction data and needle characteristic data. A puncturing navigation data generating unit generates puncturing navigation data by
(Continued)

composing tumor region data, organ region and blood vessel regions data, and data relating to the expected inserting position and insertion error region.

9 Claims, 14 Drawing Sheets

(51) Int. Cl.
A61B 6/12 (2006.01)
A61B 34/20 (2016.01)
(52) U.S. Cl.
CPC ............ *A61B 8/483* (2013.01); *A61B 8/5207* (2013.01); *A61B 34/20* (2016.02)

(56) References Cited

U.S. PATENT DOCUMENTS

| | | | |
|---|---|---|---|
| 6,055,449 A | 4/2000 | Navab | |
| 6,167,296 A * | 12/2000 | Shahidi | A61B 5/06 600/117 |
| 6,733,458 B1 * | 5/2004 | Steins | A61B 8/0833 600/461 |
| 7,491,198 B2 * | 2/2009 | Kockro | A61B 90/36 606/1 |
| 7,876,942 B2 * | 1/2011 | Gilboa | A61B 6/12 382/128 |
| 8,073,531 B2 * | 12/2011 | Goldman | A61B 5/0059 600/473 |
| 2005/0256402 A1 | 11/2005 | Kawashima et al. | |
| 2006/0140798 A1 | 6/2006 | Kutsuzawa | |
| 2006/0281987 A1 | 12/2006 | Bartesaghi et al. | |
| 2007/0049861 A1 | 3/2007 | Gundel | |
| 2007/0129631 A1 | 6/2007 | Ma et al. | |
| 2007/0167769 A1 | 7/2007 | Ikuma et al. | |
| 2008/0039723 A1 | 2/2008 | Suri et al. | |
| 2008/0123923 A1 * | 5/2008 | Gielen | G06K 9/3216 382/131 |
| 2008/0221446 A1 * | 9/2008 | Washburn | A61B 8/00 600/437 |
| 2009/0124895 A1 * | 5/2009 | Roden | A61B 6/12 600/427 |
| 2010/0022871 A1 * | 1/2010 | De Beni | A61B 8/0833 600/424 |

FOREIGN PATENT DOCUMENTS

| | | |
|---|---|---|
| JP | 5-329155 | 12/1996 |
| JP | 2000-185041 | 7/2000 |
| JP | 2003-19133 | 1/2003 |
| JP | 2004-159811 | 6/2004 |
| JP | 2004-215701 | 8/2004 |
| JP | 2004-298476 | 10/2004 |
| JP | 2006-55407 | 3/2006 |
| JP | 2007-226 | 1/2007 |
| WO | WO 2006/067676 A2 | 6/2006 |

OTHER PUBLICATIONS

Office Action dated May 28, 2013 in Japanese Patent Application No. 2007-303040 (with English translation).
Japanese Office Action dated Jun. 29, 2012 for Application No. 2007-303040 (with English translation).
U.S. Office Action dated May 9, 2018 issued in U.S. Appl. No. 12/275,886, which is the parent application of the present application.

* cited by examiner

IMAGING DIAGNOSIS APPARATUS HAVING NEEDLING NAVIGATION CONTROL SYSTEM AND A NEEDLING NAVIGATION CONTROLLING METHOD

CROSS-REFERENCE TO RELATED APPLICATIONS

This application is a continuation of and is based upon and claims the benefit under 35 U.S.C. § 120 for U.S. application Ser. No. 12/275,886, filed Nov. 21, 2008, and claims the benefit of priority from, under 35 U.S.C. § 119 from Japanese Patent Application No. 2007-303040, filed on Nov. 22, 2007. The contents of which are incorporated herein by reference.

BACKGROUND OF THE INVENTION

A. Field of the Invention

The present invention relates to an imaging diagnosis apparatus, such as an ultrasound diagnosis apparatus and a computer tomography (CT) apparatus, having a needling navigation control system and a needling navigation controlling method. More particularly, the present invention relates to an imaging diagnosis apparatus and a needling navigation controlling method that can accurately and safely navigate an invasive instrument, such as a puncturing needle, into a diagnostic target organ in the body of an object with monitoring 3-D images of the target organ and surrounding tissues such as the blood vessels that are acquired by an imaging diagnosis apparatus.

B. Background of the Invention

As described above, the puncturing needle navigation control system consistent with the present is applicable to an imaging diagnosis apparatus, such as an ultrasound diagnosis apparatus or a computer tomography (CT) apparatus. To easy understanding of the present invention, hereinafter, an ultrasound imaging diagnosis is explained for applying the puncturing needle navigation control system according to the invention.

An ultrasound imaging diagnosis apparatus transmits ultrasound and receives reflected ultrasound through a plurality of ultrasound transducers installed in an ultrasound probe to and from a target in an object in a plurality of directions in order to display the image of the target on a monitor. Since the ultrasound imaging diagnosis apparatus can easily create and display continuous two dimensional (2-D) images or continuous three dimensional (3-D) images on a monitoring screen in real time by simply contacting with the ultrasound probe onto a patient's body surface, it is widely utilized for imaging diagnosis of various bodily organs or other purposes, such as identifying the existence, location, and size of tumors.

In some circumstances for the ultrasound imaging diagnosis, it is desirable to use an invasive instrument, such as a catheter or a puncturing needle for inserting into the body of a patient in order to remove some tissue samples of an examining or treating portion, such as a tumor, or to perform other medical treatments and medicine medications. To navigate a puncturing needle into a specific position in the tumor portion with monitoring ultrasound images of the tumor, a puncturing adaptor is mounted on the ultrasound probe so as to guide a puncturing needle along a needle guide provided on the adaptor. In conventional techniques, various types of puncturing adaptors have been proposed for attaching on the ultrasound probe, for instance, as illustrated in FIGS. 14A and 14B.

FIG. 14A illustrates one example of the conventional adaptor proposed in Japanese Patent Application 2004-147984. In this technique, a puncturing adaptor 216a is attachable mounted on a head portion 211a of the ultrasound probe 201a. The head portion 211a includes a plurality of transducers. In the one end portion of the puncturing adaptor 216a, a needle guide 217 having a prescribed guiding slant is provided so that the insertion direction of the puncturing needle 218a coincides with the slice plane of an object for generating ultrasound 2-D image data. Thus, when the puncturing needle 218a is inserted into the body of the object with attaching the head portion 211a of the ultrasound probe 201a on the body surface along the needle guide 217, tip position data of the puncturing needle 218a can be displayed together with 2-D image data of a tumor portion on a monitor.

FIG. 14B illustrates another example of the conventional ultrasound probe having a puncturing adaptor configuration proposed in Japanese Patent Application 2005-342109. In the proposed configuration, a notch groove 219 is provided at one end of the head portion 211b so as to attachable connect a puncturing adaptor 216b into the groove 219. The adaptor 216b includes a needle guide. Thus, similar to the configuration illustrated in FIG. 14A, the puncturing needle 218b can be inserted into the body through the head portion 211b of the ultrasound probe 201b and the tip position of the puncturing needle 218b can be displayed together with 2-D image data of a tumor portion on a monitor.

To acquire 3-D ultrasound image data by a 1-D array ultrasound probe that includes a plurality of transducers arrayed in one dimension (1-D), it needs to move the 1-D array ultrasound probe over a 3-D area of a diagnostic target organ in the body of an object in a direction orthogonal to an array direction or rotate the 1-D array of transducers. Recently, 2-D array ultrasound probes have been used for acquiring 3-D ultrasound image data of an object. The 2-D array ultrasound probe includes a plurality of transducers arrayed in two dimensions (2-D) (i.e., an azimuth direction and an elevation direction). By using the 2-D array ultrasound probe, it has become possible to significantly shorten the volume scan time for acquiring 3-D image data of the target. 3-D image data are generated and displayed by rendering the acquired 3-D data (hereinafter, frequently referred to as "volume data"). Japanese Patent Application 2005-342109 has proposed a method for inserting a puncturing needle with monitoring the 3-D images of the volume data acquired by the 2-D array ultrasound probe.

As described above, the conventional techniques have proposed to insert a puncturing needle into a tumor portion with confirming the tip position of the puncturing needle as 2-D image or 3-D image on a monitor. However, during insertion of the puncturing needle, it is usually happened to shift the inserting direction of the puncturing needle from a prescribed slice plane for acquiring image data due to unevenness of living body tissues existing along the insertion route, i.e., differences among muscle portions and fatty portions. In such a case, the proposed conventional techniques could not confirm the inserting status of the puncturing needle on the 2-D image data. Consequently, it has difficult to accurately insert the puncturing needle into the tumor portion without injuring the surrounding tissues of the tumor portion such as the blood vessels and other organs.

To solve the above-mentioned conventional problems and defects, the present invention provides a new imaging diagnosis apparatus having a puncturing navigation control system that can navigate the accurate and safe puncturing of an invasive instrument, a catheter or a puncturing needle into a target tumor portion with monitoring ultrasound 3-D images of the puncturing target region and the surrounding regions of the blood vessels and the other organs.

According to the imaging diagnosis apparatus and the needling navigation method consistent with the present invention, since the puncturing needle can be always navigated along the eye direction while unevenness of tissues exist along the inserting direction, it becomes possible to accurately and safely inserting the puncturing needle into the tumor portion with avoiding any injuring of the surrounding blood vessels and other organs existing the target tumor portion in the body of an object. Thus, the imaging diagnosis apparatus and the method consistent with the present invention can significantly improve the efficiency and the safeness of puncturing diagnostic examinations and treatments by the insertion of a puncturing needle. Further, according to the imaging diagnosis apparatus consistent with the present invention, it can significantly reduce the burdens of the puncturing operators.

One aspect of the image diagnosis system consistent with the present invention is an ultrasound imaging diagnosis apparatus comprising:

a volume data acquiring unit configured to acquire volume data from a volume (3-D) scan region on an object;

a puncturing needle position detecting unit configured to detect a position of a puncturing needle inserted in a body of the object;

a puncturing navigation data generating unit configured to generate puncturing navigation data in order to display an anatomy in a living body that locates in an inserting direction of the puncturing needle based on the detected position of the puncturing needle; and a display unit configured to display the puncturing navigation data.

One aspect of the needling navigation controlling method for an imaging apparatus consistent with the present invention is a method for controlling puncturing operations applicable to an imaging diagnosis apparatus comprising:

acquiring volume data from a volume (3-D) scan region on an object;

detecting a position of a puncturing needle inserted in a body of the object;

generating puncturing navigation data in order to display an anatomy in a living body that locates in an inserting direction of the puncturing needle based on the detected position of the puncturing needle; and displaying the puncturing navigation data.

BRIEF DESCRIPTION OF THE DRAWINGS

The accompanying drawings, which are incorporated in and constitute part of this specification, illustrate various embodiments and/or features of the present invention, and together with the description, served to explain embodiments of the present invention. Where possible, the same reference number will be used throughout the drawings to describe the same or like parts. In the drawings.

DESCRIPTION OF THE EMBODIMENTS

In the preferred embodiment consistent with the present invention, a target tumor region for puncturing (hereinafter, "tumor region") and, major blood vessel regions (hereinafter, "blood vessel regions") and other organ region located near to the tumor region (hereinafter, "organ region") are set based on the volume data acquired by the 3-D scan on the object in order to avoid any possibility of wrong insertion by the puncturing needle into the blood vessel regions and the organ region located near the tumor region.

In the preferred embodiments of the ultrasound imaging diagnosis apparatus consistent with the present invention, based on 3-D B mode data and 3-D color Doppler data acquired by a 2-D array ultrasound probe in which a plurality of transducers are two-dimensionally arranged, volume data are generated. By using the volume data of the 3-D B mode data, the tumor region and the organ region are approximately set as a sphere or an ellipse solid. By using volume data of 3-D color Doppler data, 3-D images of the blood vessel regions themselves are set. Of course, the present invention is applicable to acquire the volume data by moving the 1-D array ultrasound probe. It is also possible to set the blood vessel region by using the volume data based on the 3-D B mode data at the time of contrast media medication instead of using 3-D color Doppler data.

Figure 1:
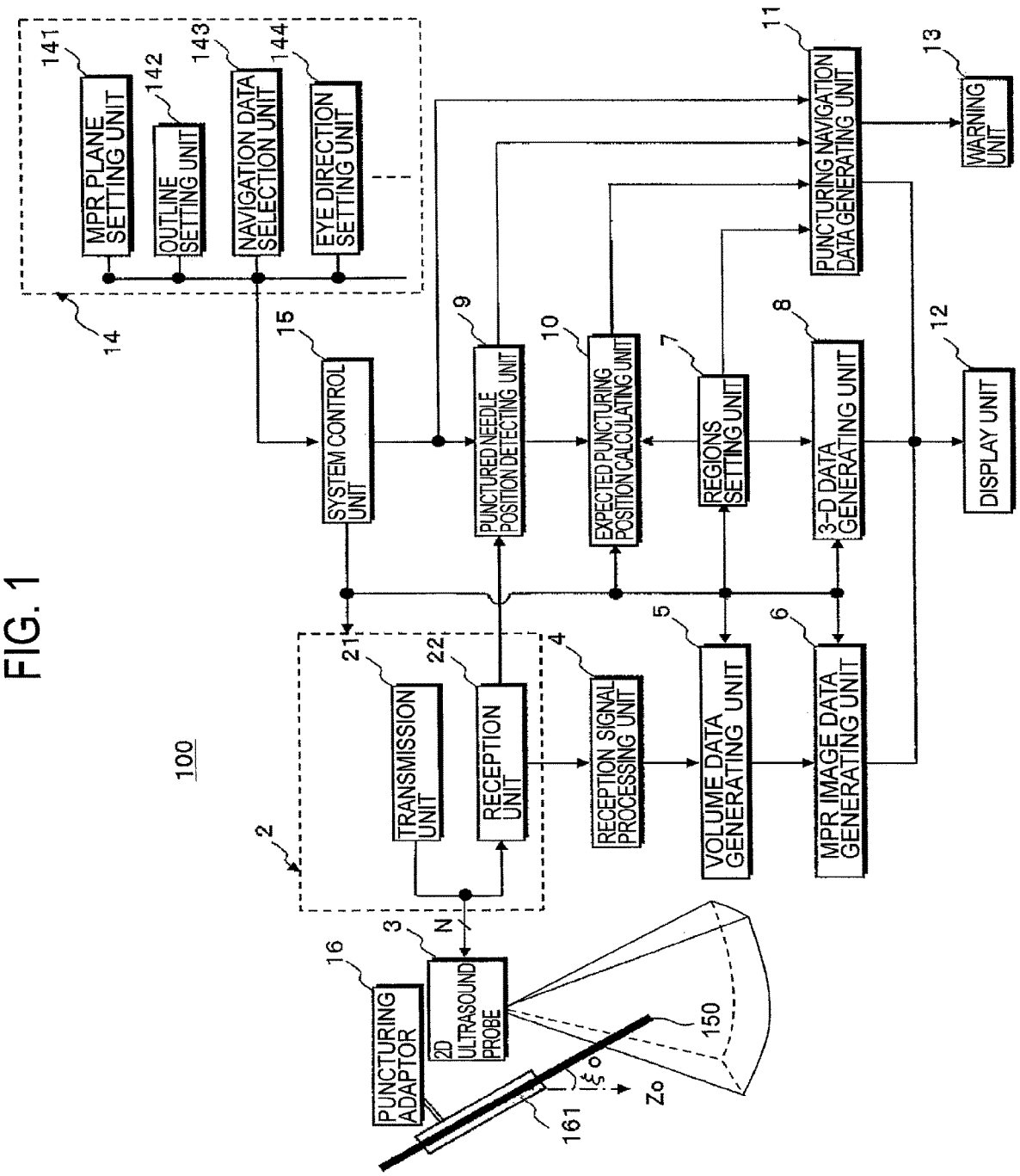
FIG. 1 is a block diagram illustrating an ultrasound imaging diagnosis apparatus in accordance with preferred embodiment of the present invention.

FIG. 1 is a block diagram of an ultrasound diagnosis system 100 in accordance with preferred embodiments applying the present invention. The ultrasound diagnosis system 100 includes a transmission/reception unit 2, a 2-D ultrasound probe 3, a receiving signal processing unit 4, a volume data generating unit 5, a multi-planar reconstruction (MPR) data generating unit 6, a region setting unit 7 and a 3-D data generating unit 8. The transmission/reception unit 2 includes a transmitting unit 21 for supplying driving signals to the transducers in the ultrasound probe 3 and a receiving unit 22 for adding receiving signals supplied from the transducers. The ultrasound probe 3 includes a plurality of 2-D arrayed transducers for transmitting ultrasound pulses (transmission ultrasound) over a 2-D area or 3-D volume of a diagnosis object portion in an object in accordance with driving signals from the transmission unit 21 and also for converting ultrasound echo signals into electric signals. The receiving signals acquired from a plurality (N) of channels of the transducers in the ultrasound probe 3 are arranged in phases and added in the receiving unit 22. The added receiving signals are processed in the receiving signal processing unit 4 in order to generate B mode image data and color Doppler data acquired by 3-D scanning over an object. The volume data generating unit 5 generates volume data by arranging the B mode data and color Doppler data so as to correspond to the ultrasound transmission and reception directions.

The ultrasound diagnosis system 100 further includes a multi-planar reconstruction (MPR) image data generating unit 6, a regions setting unit 7, a 3-D data generating unit 8, a punctured needle position detecting unit 10. The MPR image data generating unit 6 generates MPR image data of the B mode volume data at a slice plane set by an input unit 14 that is explained later. The region setting unit 7 sets a 3-D tumor region and 3-D organ regions based on outline data set by the input unit 14 against the tumor and organs located near the tumor on the MPR image data. The region setting unit 7 also sets 3-D blood vessel regions by extracting outlines from color Doppler volume data. The 3-D data generating unit 8 generates monitoring 3-D image data by composing the tumor region data, the organ region data and the blood vessel region data. The punctured needle position detecting unit 9 detects a tip position and an insertion direction of a puncturing needle 150 inserted into the body of an object along a needle guide 161 of a puncturing adaptor 16 mounted on a head portion of the 2-D ultrasound probe 3. The expected puncturing position calculating unit 10 calculates an expected tip position and an expected insertion direction of the puncturing needle to the tumor region based on various data for the puncturing needle 150 including the puncturing position and the insertion direction that will be explained later.

The ultrasound diagnosis system 100 further includes a puncturing navigation data generating unit 11, a display unit 12, a warning unit 13, an input unit 14 and a system control unit 15. The puncturing navigation data generating unit 11 generates puncturing navigation data based on a puncturing expect position data and insertion error region data in connection with tumor region data, organ region data and blood vessel region data. The display unit 12 displays MPR image data, 3-D data and puncturing navigation data. The warning unit 13 issues warning signals in a case that the organ region or the blood vessel regions in the puncturing navigation data being included in the insertion error region. The input unit 14 sets slice planes for MPR image data and outlines of the tumor and the surrounding organs on the MPR image data. The system control unit 15 totally controls the above-mentioned all units.

The ultrasound probe 3 includes a plurality (N) of 2-D arrayed transducers provided on a top surface portion of the probe. Ultrasound transmission and reception of echo ultrasound are performed by touching the top surface portion to a body surface of an object. Often, a gel is used as an intermediary between the body surface and probe surface. The transducers convert driving pulse signals to transmission signals composed of ultrasound pulses during transmission time, and convert ultrasound echoes to receiving signals during reception time. Each of the plurality N of transducers is coupled to the transmission and reception unit 2 through a multi-channel cable. A puncturing adaptor 16 is mounted on the ultrasound probe 3 in order to insert a puncturing needle 150 into the body of an object along a needle guide 161 provided on the puncturing adaptor 16. Thus, an insertion position and an insertion direction of the puncturing needle 150 are primarily determined by the needle guide 161.

In the ultrasound diagnosis system 100 in accordance with preferred embodiments of the present invention, as an example of the ultrasound probe 3, a 2-D array sector scan ultrasound probe including a plurality of N transducers is used. Of course, it is also possible to use, for example, a linear scan ultrasound probe or a convex scan ultrasound probe.

Figure 2:
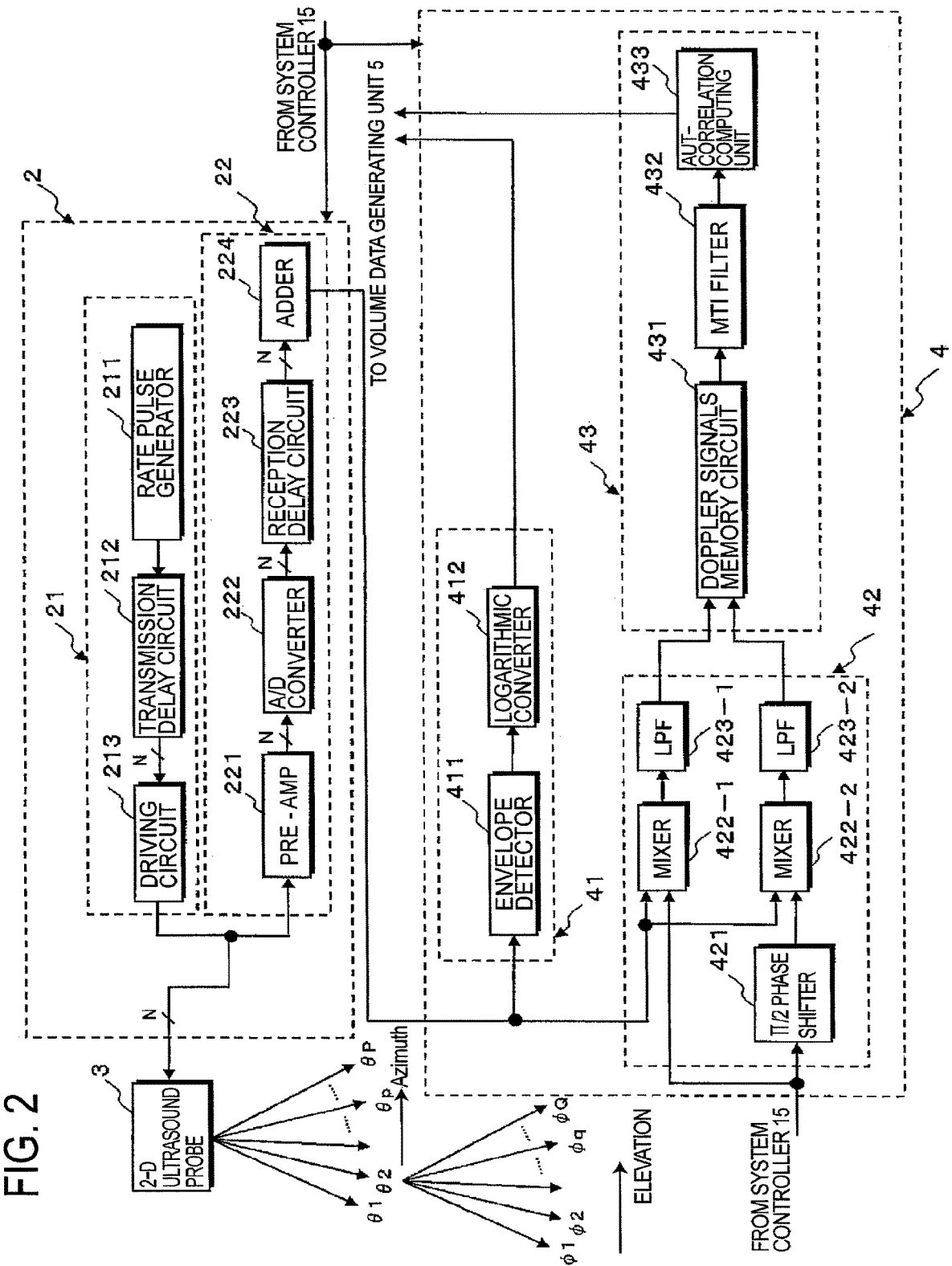
FIG. 2 is a block diagram illustrating the transmission and reception unit, and the receiving signal processing unit in the ultrasound imaging diagnosis apparatus shown in FIG. 1.

FIG. 2 is a block diagram illustrating the transmission and reception unit, and the receiving signal processing unit in the ultrasound imaging diagnosis apparatus shown in FIG. 1. The transmission and reception unit 2 includes a transmission unit 21 for supplying drive signals to the plurality of N transducers in the ultrasound probe 3 and a reception unit 22 for adding the receiving signals of N channels acquired through the plurality of transducers.

The transmission unit 21 includes a rate pulse generator 211, a transmission delay circuit 212 and a driving circuit 213. The rate pulse generator 211 generates rate pulses which determine a recycle period for transmission ultrasound. The generated rate pulses are supplied to the transmission delay circuit 212. The transmission delay circuit 212 includes a plurality of independent delay circuits of the same number of transducers N as used for transmission. The transmission delay circuit 212 gives a convergence delay time for converging the transmission ultrasound into a prescribed depth and a deviation delay time for transmitting ultrasound in a prescribed direction (θp, φq) to the rate pulses and supplies to the driving circuit 213.

The reception unit 22 includes a plurality of (N channels) of pre-amplifiers 221, a plurality of (N channels) of A/D converters 222, a plurality of (N channels) of reception delay circuits 223 and a plurality of (N channels) of adders so as to obtain a sufficient S/N ratio by amplifying weak signals. The plurality of (N channels) of reception signals amplified in the pre-amplifier 221 are converted to digital signals in the A/D converter 222 and supplied to the reception delay circuit 223. The reception delay circuit 223 gives each of the reception signals outputted from the A/D converter 222 a convergence delay time for converging reception ultrasound from a prescribed depth and a deviation delay time for setting a reception directivity to a predetermined direction (θp, φq). The reception signals acquired from the prescribed direction (θp, φq) are added in the adder 224.

FIG. 3A illustrates an ultrasound probe 3 having 2-D array transducers Trs and an ultrasound transmission/reception position P (r, θp, φq). The ultrasound probe 3 has a center axis (z-axis). The ultrasound transmission/reception position P (r, θp, φq) locates at a distance r from a surface of the transducers Trs in an $X_0$-axis (azimuth) direction and a $Y_0$-axis (elevation) direction. FIG. 3B illustrates a projected position P on an $X_0$-$Z_0$ plane transmitting and receiving ultrasound at an angle θp in the $X_0$-axis (azimuth) direction from the $Z_0$-axis. FIG. 3C illustrates a projected position P on the $Y_0$-$Z_0$ plane transmitting and receiving ultrasound at an angle φq in the $Y_0$-axis (elevation) direction from the $Z_0$-axis.

The reception signals processing unit 4 shown in FIG. 2 includes a B mode data generating unit 41 for generating B mode data by processing the received signals supplied from the adders 224 in the reception unit 22, a Doppler signals detection unit 42 for detecting the Doppler signals by orthogonally detecting the phases of the received signals and a color Doppler data generation unit 43 for generating color Doppler data reflecting blood flow data in the main blood vessel based on the detected Doppler signals. The B mode data generating unit 41 includes an envelope detector 411 for detecting the envelope of the reception signals supplied from the adder 224 in the reception unit 22 and a logarithmic converter 412 for generating B mode data by converting the amplitude of the envelope detected reception signals. It is possible to replace of the positions of the envelope detector 411 and the logarithmic converter 412.

The Doppler signal detection unit 42 includes a π/2 phase converter (shifter) 421, mixers 422-1 and 422-2 and low pass filters (LPFs) 423-1 and 423-2 in order to detect Doppler signals by orthogonally detecting the phases of the reception signals supplied from the adders 224 in the reception unit 22.

The color Doppler data generation unit 43 includes a Doppler signals memory circuit 431, a MTI filter 432 and an auto-correlation computing unit 433. The Doppler signals memory circuit 431 stores Doppler signals detected by the Doppler signals detection unit 42. The MTI filter 432 removes Doppler clutter components that are generated due to fixed reflectors in an organ and breathing movements or pulse movements of the organ from the detected Doppler signals. The auto-correlation computing unit 433 generates color Doppler data by using three kinds of characteristic values, i.e., a mean velocity value, a dispersing value and a power value of blood flows based on the self-correlation value.

Figure 4:
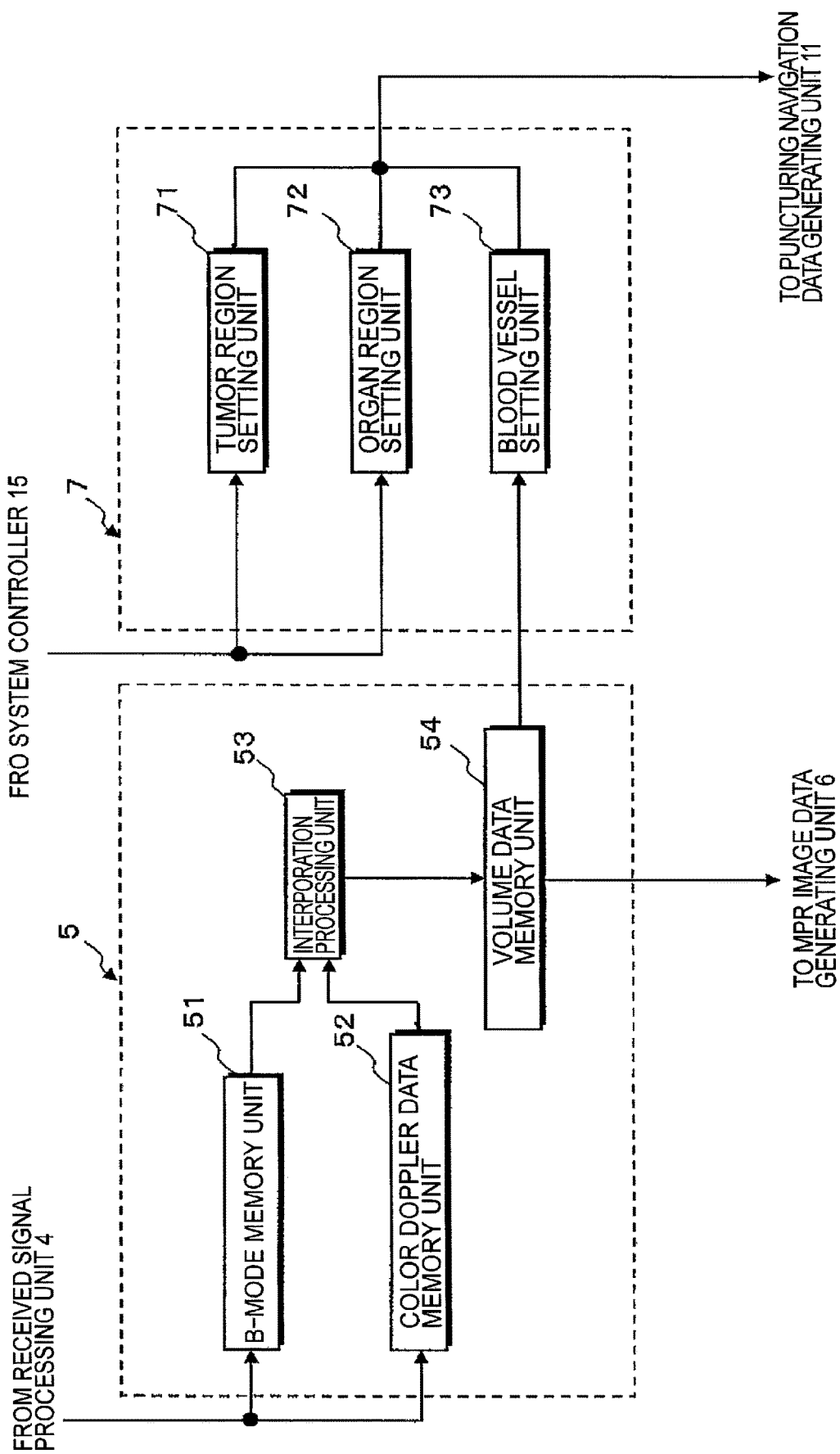
FIG. 4 is a block diagram illustrating the volume data generating unit, and the region setting unit in the ultrasound imaging diagnosis apparatus shown in FIG. 1.

FIG. 4 is a block diagram illustrating a construction of the volume data generating unit 5 and the regions setting unit 7 shown in FIG. 1. The volume data generating unit 5 includes a B mode data memory unit 51, a color Doppler data memory unit 52, an interpolation processing unit 53 and a volume data memory unit 54. The B mode data memory unit 51 in the volume data generating unit 5 successively stores B mode data generated by the B mode data generating unit 41 (FIG. 2) based on the acquired reception signals by 3-D scans over the object with affixing ultrasound transmission/reception directions as attached data. Similarly, the color Doppler data memory unit 52 in the volume data generating unit 5 successively stores color Doppler data generated by the color Doppler data generating unit 43 based on the acquired reception signals with affixing ultrasound transmission/reception directions as attached data.

The interpolation processing unit 53 generates 3-D B mode data by reading out a plurality of B mode data at a prescribed time phase in order to arrange the plurality of B mode data so as to correspond to their transmission/reception directions. The interpolation processing unit 53 further generates B mode volume data comprised of equal interval voxels by performing interpolation processes for the unequal interval voxels of the generated B mode data.

Similarly, the interpolation processing unit 53 generates 3-D color Doppler data by reading out a plurality of color Doppler data at a prescribed time phase so as to arrange the plurality of color Doppler data corresponding to each transmission/reception directions. The interpolation processing unit 53 further generates color Doppler volume data by performing interpolation processes for the 3-D color Doppler data. The generated 3-D color Doppler data and the 3-D color Doppler data are stored in the volume data memory unit 54.

Turning to FIG. 1, the B mode volume data stored in the volume data memory unit 54 in the volume data generating unit 5 are read out and supplied to the MPR image data generating unit 6. The MPR image data generating unit 6 sets a plurality of MPR planes on the B mode volume data based on MPR planes data supplied from the MPR planes setting unit 141 in the input unit 14 as explained later. MPR image data are generated by extracting voxels of each B mode volume data corresponded to each of the plurality of MPR planes.

Figure 3:
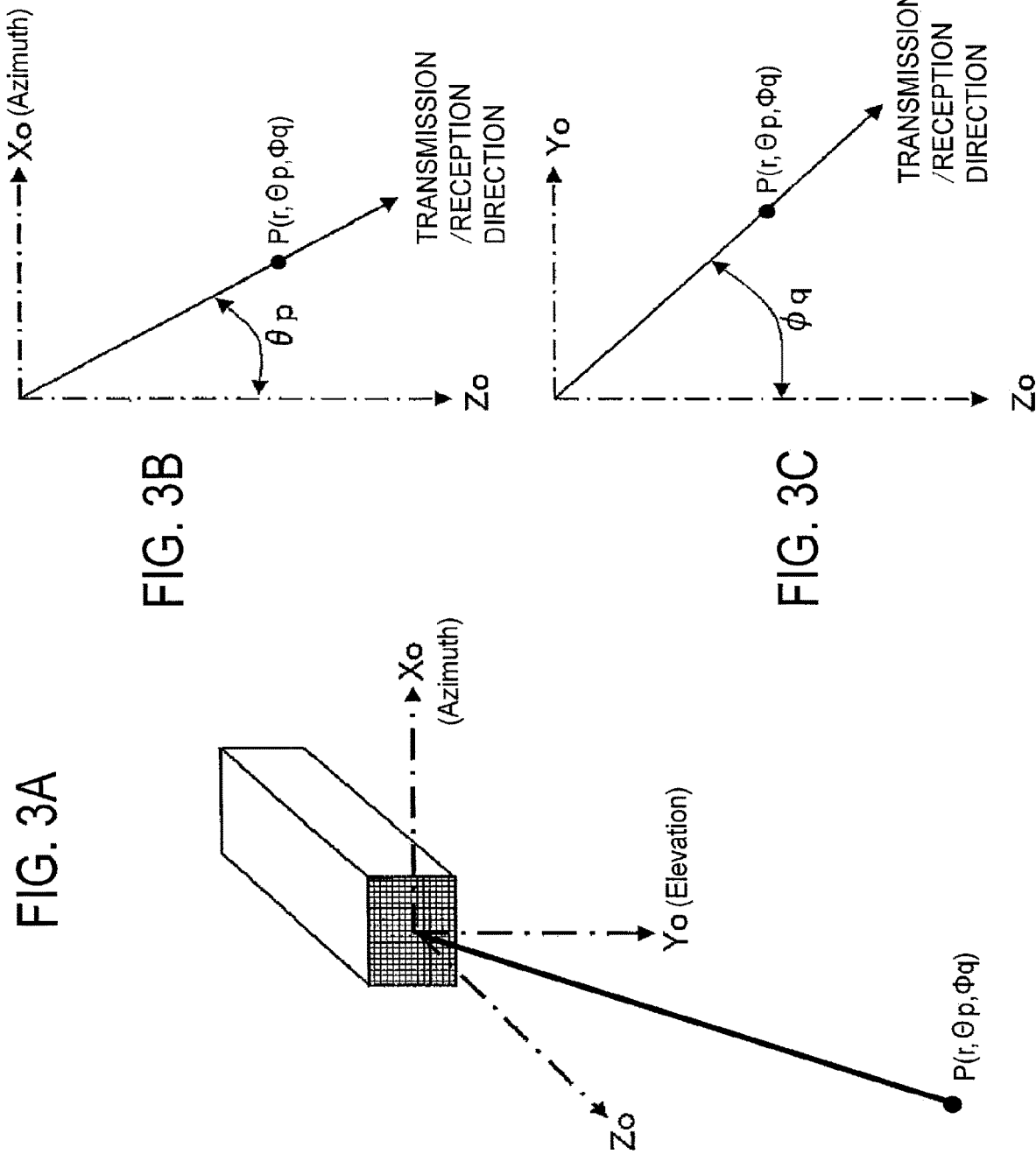
FIG. 3A illustrates the direction of ultrasound transmission and reception in a volume scan by 2-D array transducers provided in an ultrasound probe.
FIG. 3B illustrates the direction of ultrasound transmission and reception projected on the x-z plane in the volume scan shown in FIG. 3A.
FIG. 3C illustrates the direction of ultrasound transmission and reception projected on the y-z plane in the volume scan shown in FIG. 3A.
Figure 5A:
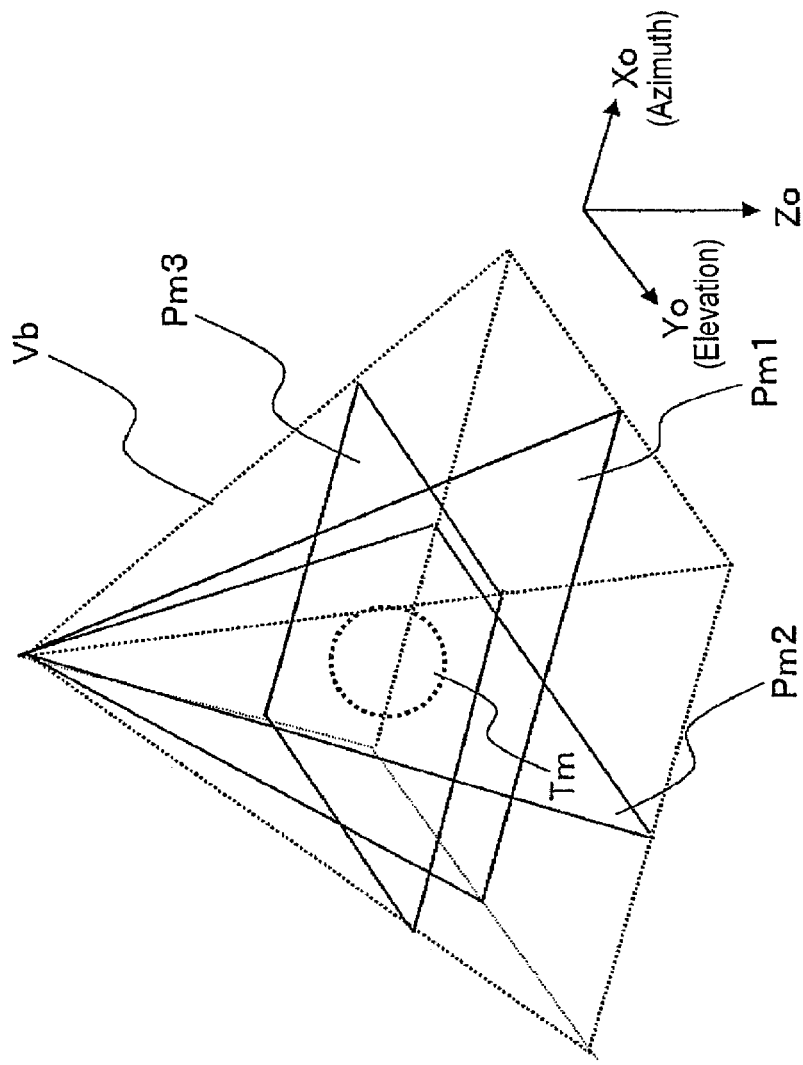
FIG. 5A illustrates the three multi planar reconstruction (MPR) planes set on the B-made volume data that includes the target portion generated by the ultrasound imaging diagnosis apparatus shown in FIG. 1.

FIG. 5A illustrates an example the plurality of MPR planes set on the B mode volume data including the tumor portion Tm. For instance, three MPR planes Pm1 to Pm3 are set on the B mode volume data Vb including the tumor portion Tm. In this embodiment, MPR plane Pm1 is set in parallel to the X0-Z0 plane. MPR plane Pm2 is set in parallel to the Y0-Z0 plane. MPR plane Pm3 is set in perpendicular to the center axis Z0 of the ultrasound probe 3 as shown in FIG. 3. Thus, X0 shows an azimuth direction, and Y0 shows an elevation direction. Usually, these three MPR planes Pm1 to Pm3 are orthogonally set with each others so that each of crossing points intersects at a substantial center position of the tumor portion Tm.

Figure 5B:
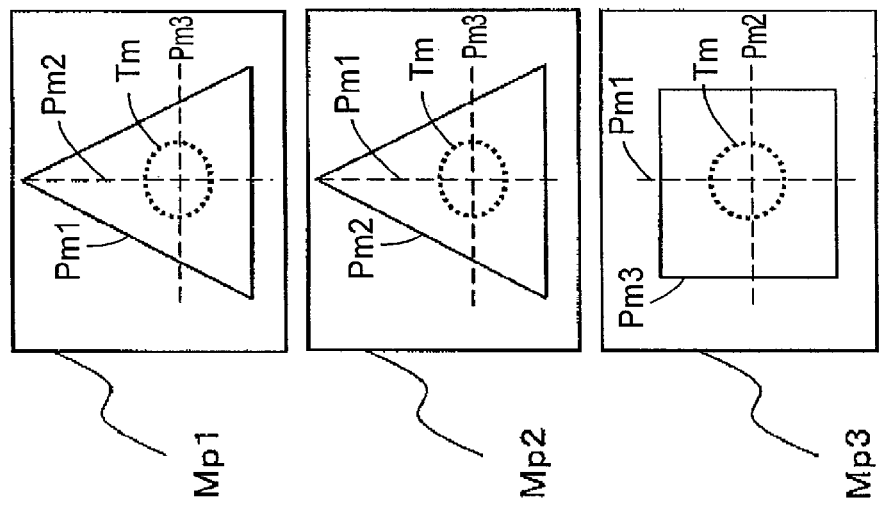
FIG. 5B illustrates three MPR image data generated at each of three MPR scan planes shown in FIG. 5A.

FIG. 5B illustrates three MPR image data Mp1 to Mp3 that are respectively generated at each of the three MPR planes Pm1 to Pm3.

FIG. 4 illustrates a practical constriction of the regions setting unit 7 shown in FIG. 1. The includes a tumor region setting unit 71, an organ region setting unit 72 and a blood vessel region setting unit 73. The tumor region setting unit 71 sets a 3-D tumor region based on the outline data set by the outline setting unit 142 in the input unit 14 to the respective tumor portion Tm in the three MPR image data Mp1 to Mp3 in the MPR image data generating unit 6 and displayed on the display unit 12. For instance, the 3-D tumor region is approximated to a wire framed sphere body or an ellipse body. Similarly, the organ region setting unit 72 sets 3-D organ region approximated by a sphere body or an ellipse body to major organs located near to the tumor portion Tm in MPR image data Mp1 to Mp3 based on the outline data set by the outline setting unit 142.

On the other hand, the blood vessel region setting unit 73 reads out color Doppler volume data stored in the volume data memory unit 54 in the volume data generating unit 5. Based on the blood flow data in the color Doppler volume data, the main blood vessels which run the neighborhood of tumor portion Tm are set as three-dimensional (3-D) blood vessel region.

Figure 6:
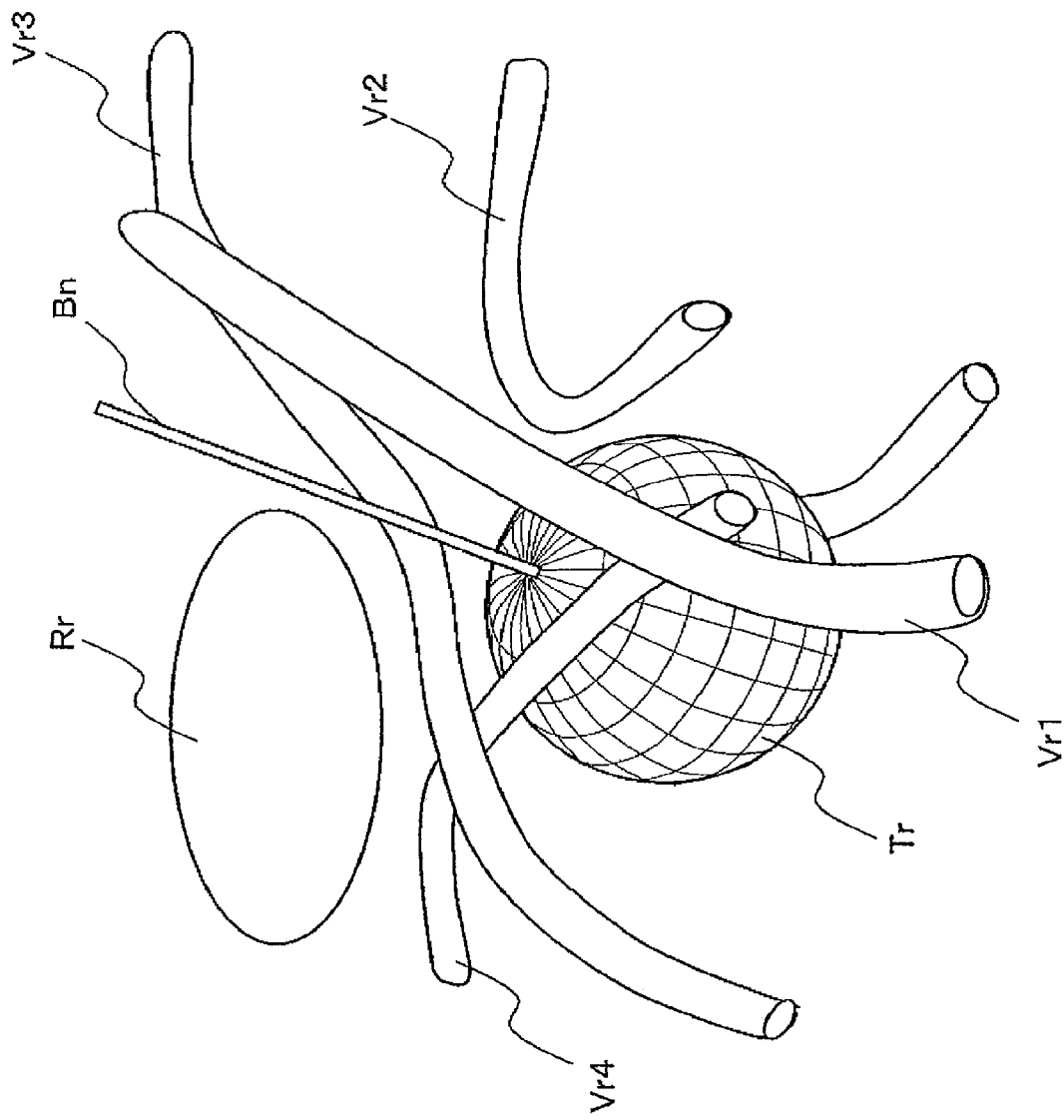
FIG. 6 illustrates 3-D data of tumor region, organ region and blood vessel regions that are generated by the 3-D data generating unit in the embodiment of the ultrasound imaging diagnosis apparatus shown in FIG. 1.

The 3-D data generating unit 8 shown in FIG. 1 generates monitoring 3-D data by composing the respective 3-D data of the tumor region, the organ region and the blood vessel regions, a tip position data of the puncturing needle 150 and the inserting direction data of the puncturing needle that are detected by the puncturing needle position detecting unit 9. FIG. 6 illustrates an example of the 3-D data generated by the 3-D data generating unit 8. The tumor region Tr is approximated by the sphere of a wired frame. The organ region Rr of circumference main internal organs, such as a bone, is approximated by a rotation ellipse. Four blood vessel regions Vr1 to Vr4 are shown so as to run the neighborhood of tumor portion Tm. Further, a puncturing marker Bn showing the inserting direction and the expected inserting position of the puncturing needle 150 are generated as 3-D data by composing the tip position data of the puncturing needle 150 and the inserting direction data of the puncturing needle that are detected by the puncturing needle position detecting unit 9.

To display these 3-D data, the eye direction setting unit 144 in the input unit 14 can arbitrarily set a desired eye direction. Thus, the eye direction setting unit 144 can set the eye direction so that the inserting direction or the expected inserting position of the puncturing marker Bn to the tumor region Tr can be observed without blocking by the blood vessel region Vr and/or the organ region Rr.

The puncturing needle position detecting unit 9 (FIG. 1) detects the tip position and inserting direction of the puncturing needle 150 at the just before the insertion to the object and during the insertion. The puncturing needle position detecting unit 9 receives slant angle data of the needle guide 161 that are provided from the system control unit 15 in accordance with the identification data of the puncturing adaptor 16 that is inputted through the input unit 14. Based on this slant angle data, he puncturing needle position detecting unit 9 detects the inserting position and inserting direction of the puncturing needle 150 just before the insertion.

With performing 3-D scan on the object, the puncturing needle position detecting unit 9 further detects the tip position of the puncturing needle 150 during insertion into the body is detected based on the ultrasound reflected from the tip portion of the puncturing needle 150. The inserting direction of the puncturing needle 150 is detected based on the time variation of the tip position. In order to detect the tip position of the puncturing needle 150 in high accuracy, it is desirable to form minute irregularity on the tip surface of the puncturing needle 150 so as to acquire a bigger amplitude of the ultrasound reflected from the tissues of the living body.

It is also possible to detect the tip position of the puncturing needle 150 based on the insertion distance of the puncturing needle that is detected by a sensor provided on the needle guide. It is applicable to use an encoder that mechanically acts on the puncturing needle 150 as the sensor. Of course, an optical sensor or a magneto metric sensor is also possible to use as a sensor. When the puncturing needle 150 is freely inserted without using the needle guide 161, it may be possible to detect the tip position of the needle by using a position sensor mounted on a portion of the puncturing needle 150.

The expected inserting position calculating unit 10 (FIG. 1) calculates a distance between the tip position and the tumor region, i.e., a distance between the tip portion of the puncturing needle and the tumor region by receiving the data of the tip position and inserting direction of the puncturing needle 150 at the just before the insertion to the object and during the insertion. Based on these distance data between the tip position and the tumor region and the inserting direction data of the puncturing needle 150, the expected inserting position to the tumor region is calculated by assuming that the puncturing needle 150 goes straight into the tissue of the living body.

The expected inserting position calculating unit 10 further calculates an insertion error region by presuming a possible bent degree of the puncturing needle 150 during the insertion based on the various data, such as the distance data between the needle tip and the tumor region, material data of the puncturing needle, such as a hardness of the puncturing needle, and living body data, such as tissue hardness of the living body of the object that are supplied from the system control unit 15. Based on the presumed bent degree of the puncturing needle, a possible error region of the expected inserting position is calculated as the insertion error region.

The puncturing navigation data generating unit 11 (FIG. 1) generates puncturing navigation data based on the tumor region data, blood vessel region data and organ region data that are supplied from the regions setting unit 7 and the data of the expected inserting position and insertion error region that are supplied from the expected inserting position calculating unit 10.

Figure 7:
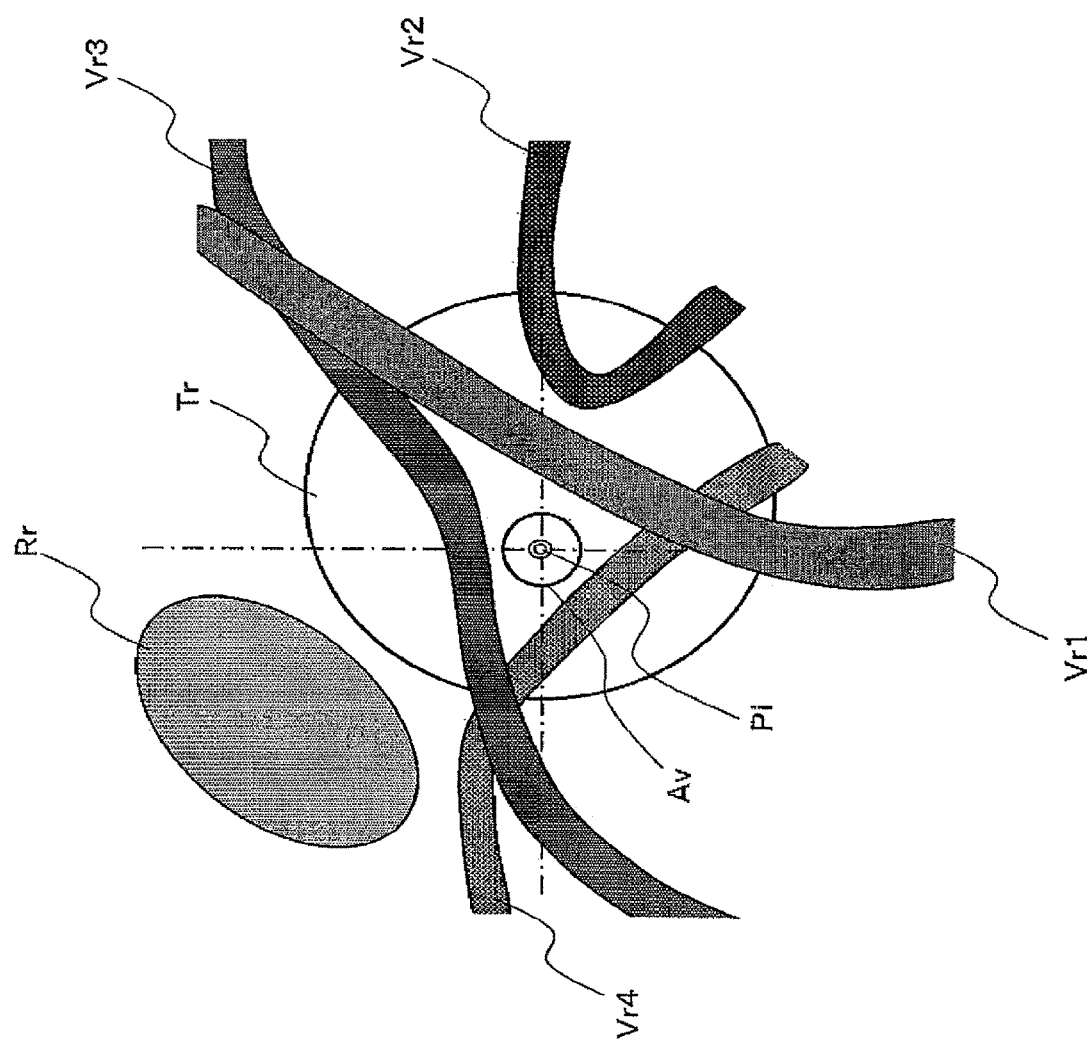
FIG. 7 illustrates an example of the puncturing navigation data at a front of the tumor region just before the insertion of the puncturing needle in the embodiment shown in FIG. 6.

FIG. 7 illustrates a practical example of the puncturing navigation data when the puncturing needle 150 is mounted along the needle guide 161 of the puncturing adaptor 16. The puncturing navigation data are generated by performing rendering process or projecting process of these eye direction data of the tumor region Tr, blood vessel regions Vr1 to Vr4 that locate in a depth range between a body surface of the object and the tumor region Tr and the organ region Rr based on the slant angle data ξo (FIG. 1) supplied from the system control unit 15, and also by superimposing the expected inserting position data Pi and insertion error region data Av along the insertion direction as the eye direction on these processed data.

Figure 8C:
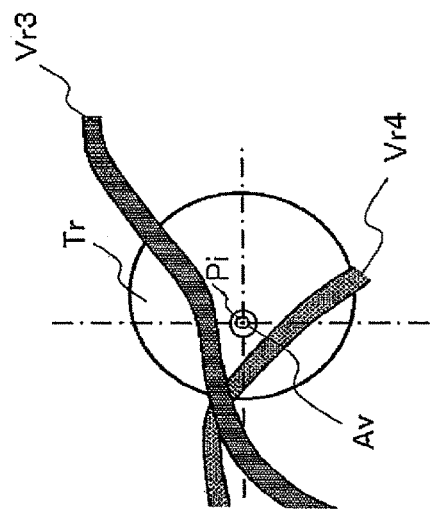
FIGS. 8A-8E illustrate examples of practical puncturing navigation data in each of proceedings of the insertion of the puncturing needle into the body of the object.
Figure 8B:
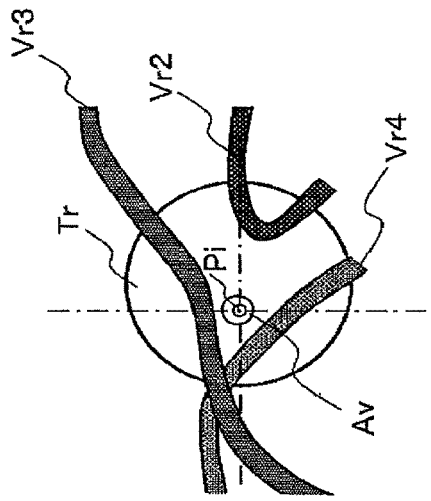
Figure 8E:
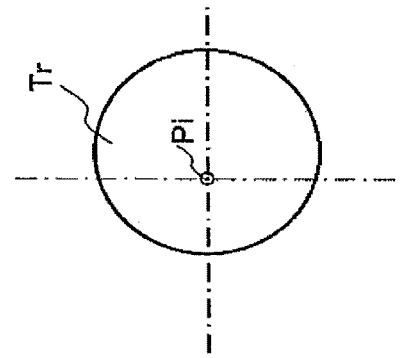
Figure 8A:
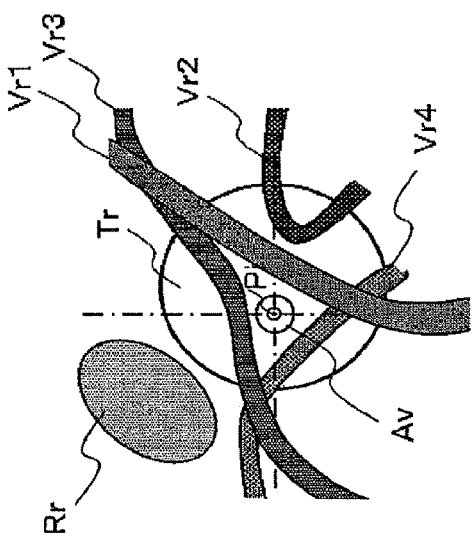

FIGS. 8A to 8E illustrate practical examples of the puncturing navigation data that are acquired in accordance with successive inserting depths of the puncturing needle 150 into the object body along the inserting direction as an eye viewing direction. FIG. 8A illustrates the puncturing navigation data that is generated just after insertion of the puncturing needle 150 into a body surface of the object. At this time, as shown in FIG. 8A, the puncturing navigation data including the blood vessel regions Vr1 to Vr4 and the organ region Rr that are exist in a depth region between the body surface of the object and the tumor region Tr.

Figure 8D:
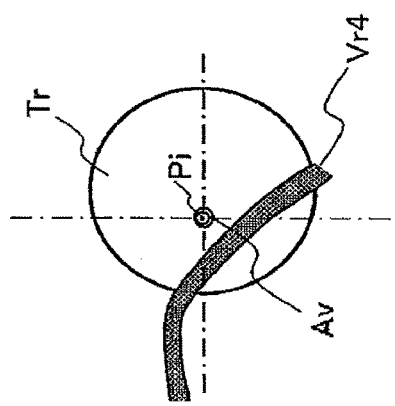

FIG. 8B-8E show the successive variations of the puncturing navigation data depend on the insertion depths of the puncturing needle. FIG. 8B illustrates a first stage in which the blood vessel region Vr1 and the organ region Rr are disappeared from the puncturing navigation data since they exist in the nearest distance from the body surface. Furthermore, as the insertion depth of the puncturing needle increases, the blood vessel region Vr2 near to the body surface, the blood vessel region Vr3 and the blood vessel region Vr4 are disappeared in order from the puncturing navigation data in accordance with the increase of the insertion depth of the puncturing needle, as illustrated in FIGS. 8C and 8D. As the distance from the tip position of the puncturing needle 150 to the tumor region Tr is shortened, the insertion error region Av also gradually reduces depending on the insertion depth. When the top portion of the puncturing needle 150 reaches to the surface of the tumor region Tr, the insertion error region Av formed around the expected inserting position Pi is also disappeared as illustrated in FIG. 8E.

Figure 9:
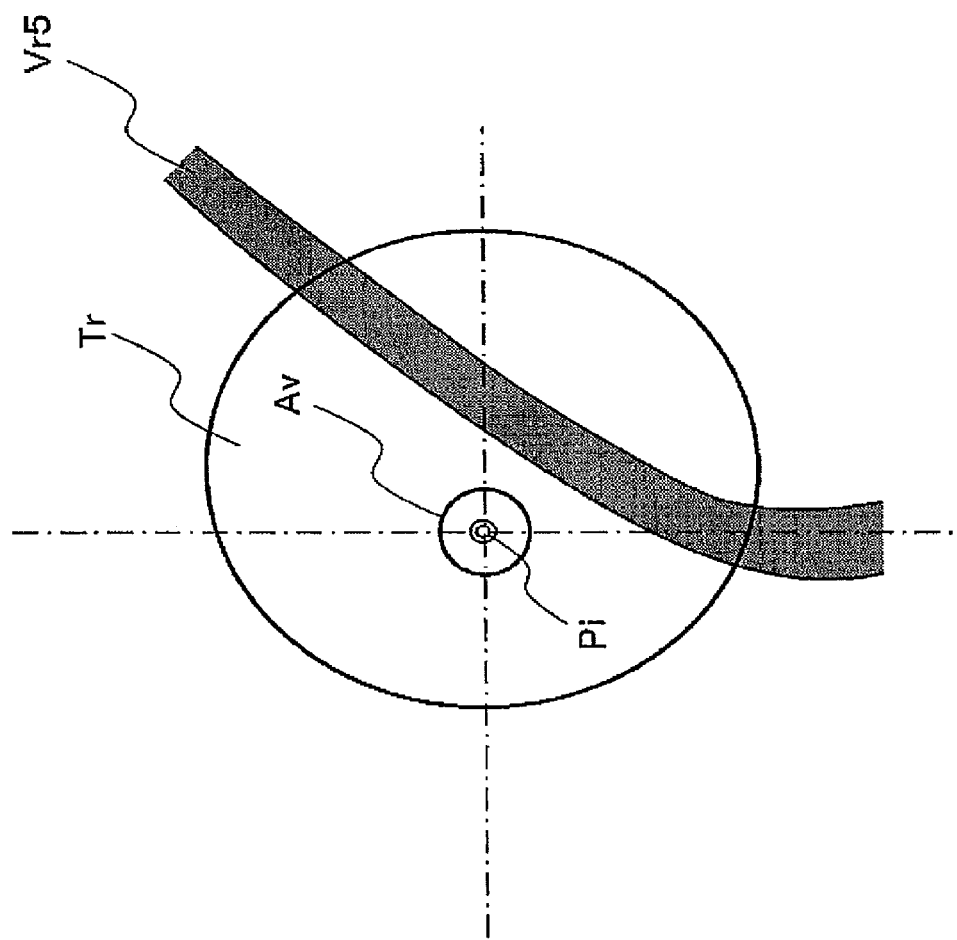
FIG. 9 illustrates the puncturing navigation data at the behind of the tumor region before insertion or during insertion of the puncturing needle in the embodiment shown in FIG. 6.

FIG. 9 illustrates the puncturing navigation data that is generated before or during insertion of the puncturing needle at the behind of the tumor region Tr. The puncturing navigation data is generated by composing the tumor region data Tr supplied from the puncturing needle position detecting unit 9, a blood vessel region data Vr5 that locates the behind of the tumor region Tr, the expected inserting position data Pi and the insertion error region data Av.

Figure 10A:
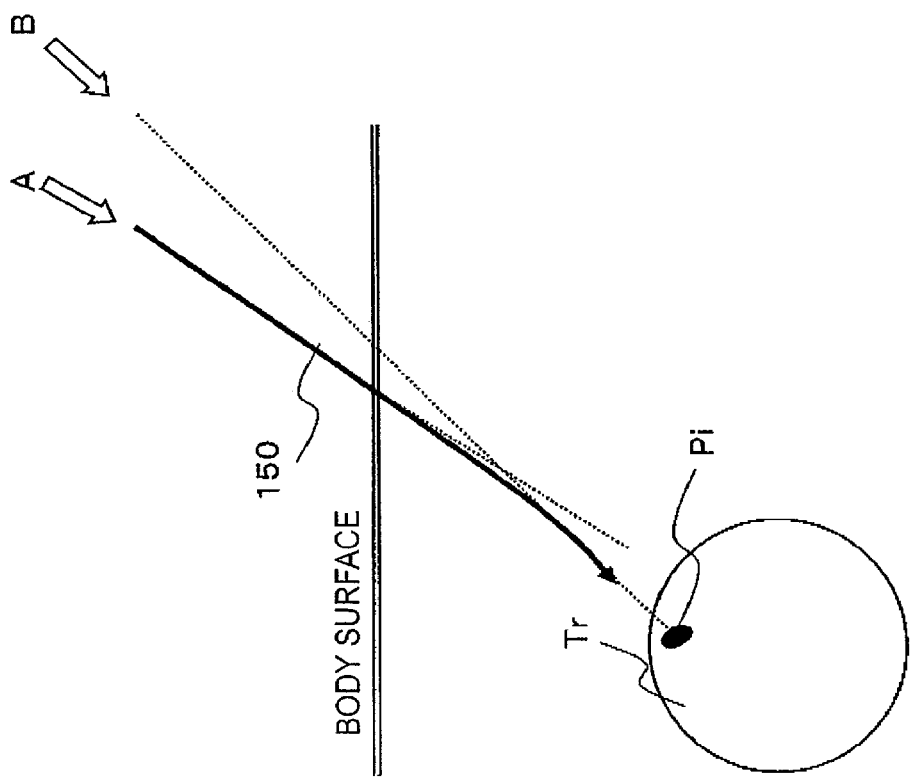
FIG. 10A illustrates an eye direction of the puncturing navigation data before insertion of a puncturing needle at an initial setting.
Figure 10B:
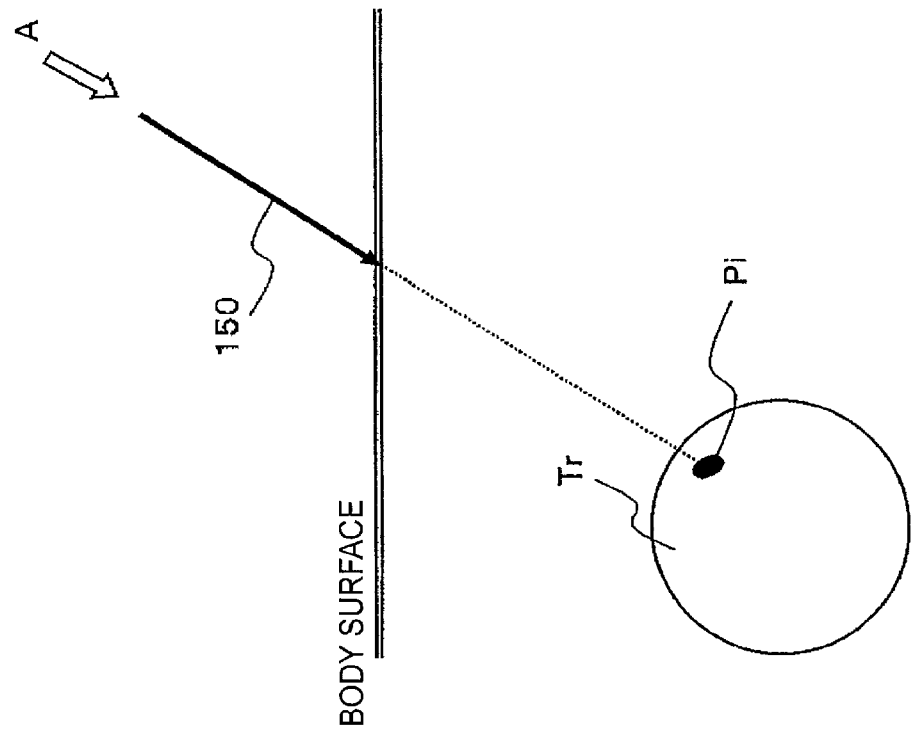
FIG. 10B illustrates a renewed eye direction of the puncturing navigation data due to flexion of the puncturing needle in the body of the object.

During the generation of the puncturing navigation data, the eye direction is set in accordance with the insertion direction of the puncturing needle 150. For example, FIG. 10A illustrates an eye direction of the puncturing navigation data before insertion of a puncturing needle at an initial setting time. As shown in FIG. 10A, when the inserting direction of the puncturing needle 150 is initially set along the direction A so as to face the expected inserting position Pi of the tumor region Tr, the eye direction of the puncturing navigation data before the insertion coincides with the direction A. If the inserting direction is bent due to flexion of the puncturing needle into the body of the object, the eye direction of the puncturing navigation data during the insertion is also renewed to the direction B as illustrated in FIG. 10B.

The display unit 12 (FIG. 1) displays MPR image data generated in the MPR image data generating unit 6 (FIG. 5B), 3-D data generated in the 3-D data generating unit 8 (FIG. 6) and the puncturing navigation data generated in the puncturing navigation data generating unit 11 before and during the insertion of the puncturing needle (FIGS. 7-9).

The display unit 12 includes a display data generating circuit, a conversion circuit and a monitor (not shown). The display data generating circuit in the display unit 12 generates displaying data by superimposing supplementary data, such as object data to the MPR image data, 3-D data and puncturing navigation data. The conversion circuit in the display unit 12 executes D/A conversions and television format conversions of the display data so as to display the display data on the monitor. On the monitor, it is desirable to display the blood vessel region data Vr by using different colors or brightness in accordance with the depth of the blood vessel region. For instance, each of the blood vessel regions Vr1 to Vr4 illustrated in FIG. 7 are respectively displayed in a white, a yellow, a orange and a red color, respectively. The colored display can easily recognize each depth of the blood vessel regions. It is also possible to display the tumor region, the organ region and the blood vessel regions in each of different colors or brightness in order to easily recognize each of the regions.

Figure 11A:
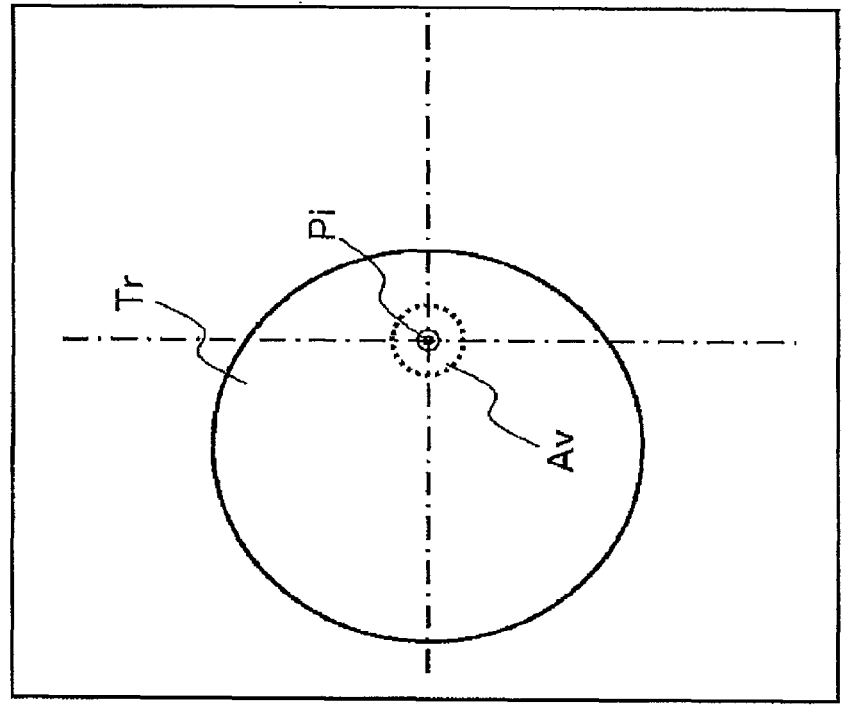
FIG. 11A illustrates an example of display of the puncturing navigation data in which a center of the tumor region locates at a center of the monitor.
Figure 11B:
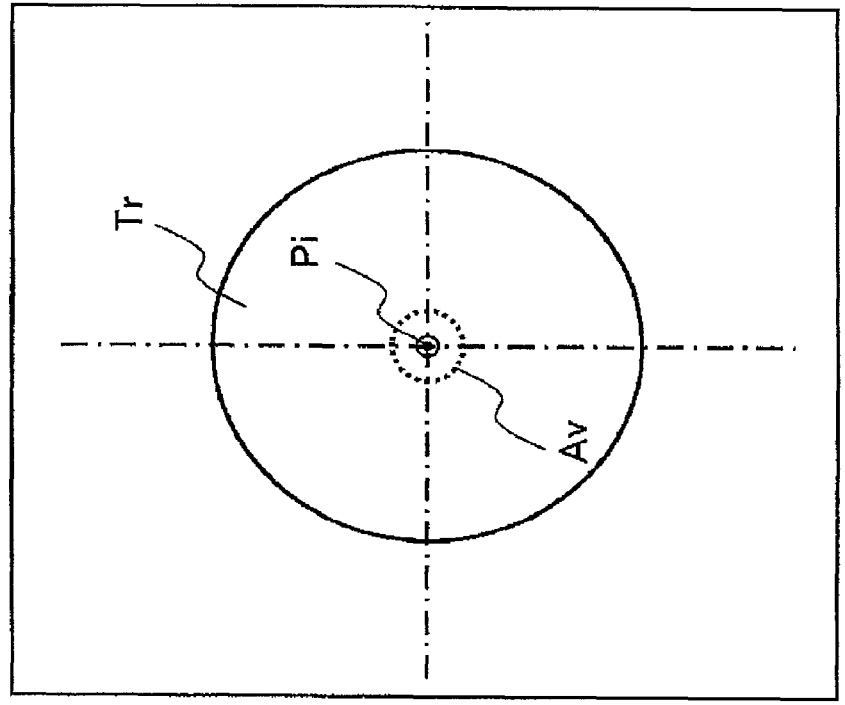
FIG. 11B illustrates an example of display of the puncturing navigation data in which the expected inserting position to the tumor region locates at a center of the monitor.

As illustrated in FIGS. 11A and 11B, in order to display the puncturing navigation data on the monitor, it is desirable to display so as that a center of the tumor region Tr or an expected inserting position Pi of the tumor region Tr locates at a center portion of the monitor. However, such a positioning of the location is not mandatory. When the tip portion of the puncturing needle 150 reached to the tumor region Tr, i.e., when the distance between the tip portion of the puncturing needle and the tumor region becomes zero, the inserted position to the tumor region Tr or the surrounding portion of the inserted position is blinked on the display.

If the organ region Rr or blood vessel region Vr in the puncturing navigation data overlap or contact to the insertion error region Av for the expected inserting position Pi, the warning unit 13 (FIG. 1) generates warning signals in order to urge a re-setup of the puncturing conditions including the inserting position and inserting direction of the puncturing needle 150. For example, the warning unit 13 informs the warning signals to an operator by using such as a warning lamp, a warning buzzer or a display of warning indications.

Figure 12A:
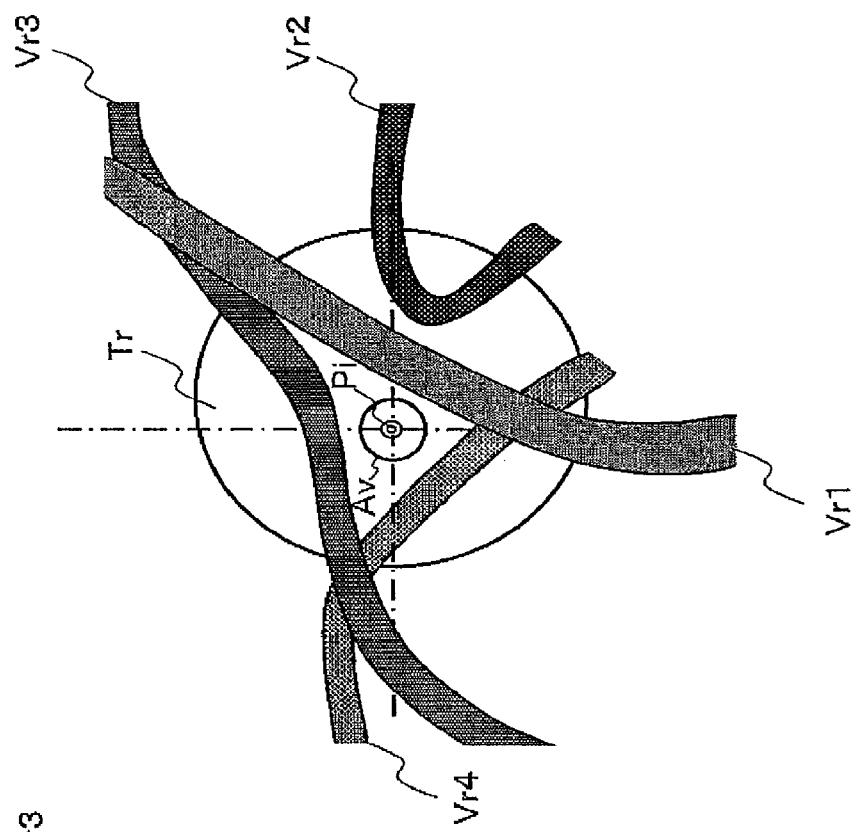
FIG. 12A illustrates a practical example of the puncturing navigation data displayed on a monitor in which the insertion error region overlaps on one portion of a plurality of blood vessel regions in front of the tumor region.
Figure 12B:
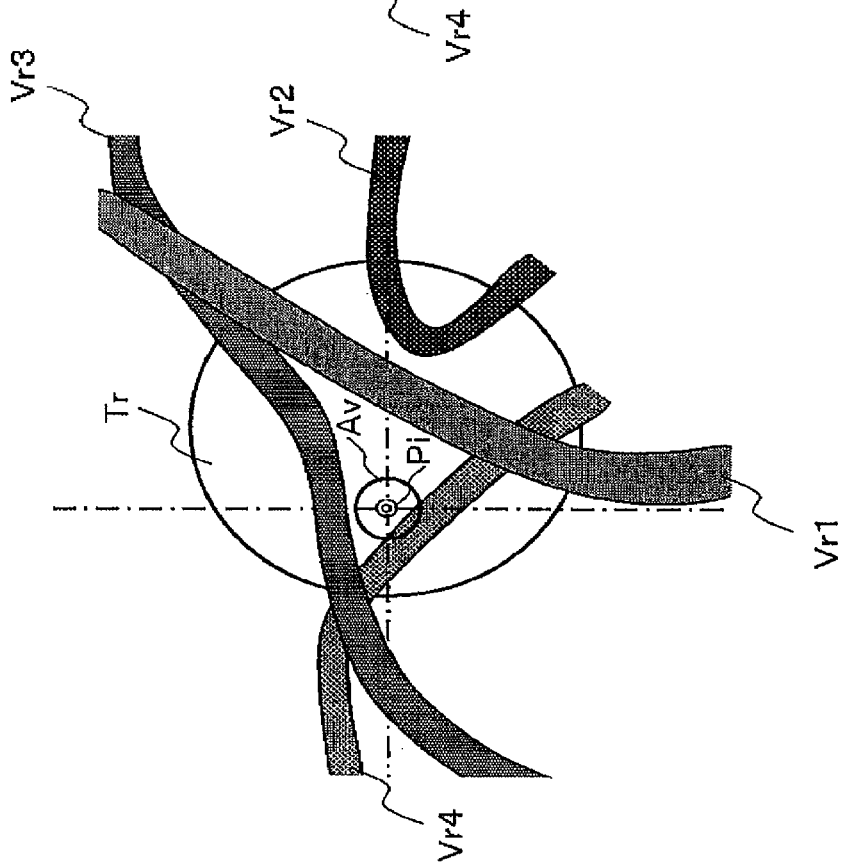
FIG. 12B illustrates an example of a renewal status of the inserting direction of the puncturing needle by an operator who renewed the inserting direction of the puncturing needle until acquisition of the puncturing navigation data in that the plurality of blood vessel regions do not overlap on the insertion error region.

As illustrated in FIG. 12A, if the puncturing navigation data displayed on the display unit 12 shows a status that one portion of the blood vessel regions Vr1 to Vr4 overlapped onto the insertion error region Av, the warning unit 13 issues warning signals so as to indicate an accidental possibility of wrong puncturing into the main blood vessels that are running the neighborhood of the tumor region Tm. During insertion of the puncturing needle with observing the puncturing navigation data, when the warning signals are issued, the operator renews the inserting direction of the puncturing needle 150 until that the puncturing navigation data shows no overlapping between the insertion error region Av and the blood vessel regions Vr1 to Vr4 as shown in FIG. 12B. The puncturing navigation data in FIG. 12B displays the status that the insertion error region Av does not overlap with any of the blood vessel regions Vr1 to Vr4. Thus, after confirming a safety of the insertion on the puncturing navigation data after the renewal, the insertion of the puncturing needle 150 into the object is started.

FIG. 12A describes the puncturing navigation data at the front area of the tumor region. It is also possible to change the inserting direction of the puncturing needle 150 with confirming safety by observing the puncturing navigation data at the behind of the tumor region, i.e., a deeper position than the tumor region Tr. In this case, as explained later, the support data selection unit 143 in the input unit 14 performs a display change of the puncturing navigation data at the front of the tumor region tumor region and the puncturing navigation data at the behind of the tumor region on the display unit 12.

The input unit 14 includes an MPR plane setting unit 141, an outline setting unit 142, a support data selection unit 143 and an eye direction setting unit 144. The MPR plane setting unit 141 sets one or a plurality of MPR plane against the volume data acquired through the 3-D scan on the object. The outline setting unit 142 sets outlines of the tumor and major organs existing near to the tumor in the MPR image data generated at the plurality of MPR planes. The support data selection unit 143 selects the puncturing navigation data at the front and the backward of the tumor region. The eye direction setting unit 144 sets an eye direction of the 3-D data These setting operations are executed by using input devices, such as, a display panel, a keyboard unit, selection buttons or a mouse. Thus, the selected input devices set the volume data acquisition conditions, display conditions for displaying the MPR image data, 3-D data and puncturing navigation data. The input devices further set various command signals.

The system control unit 15 shown in FIG. 1 includes a central processing unit (CPU) and a memory (not shown). The memory in the system control unit 15 stores above-mentioned various data that are inputted, selected and set by each of the devices of the input unit 14. The CPU in the system control unit 15 controls each of the units in the ultrasound imaging diagnosis apparatus 100 so as to generate and display the puncturing navigation data.

Figure 13:
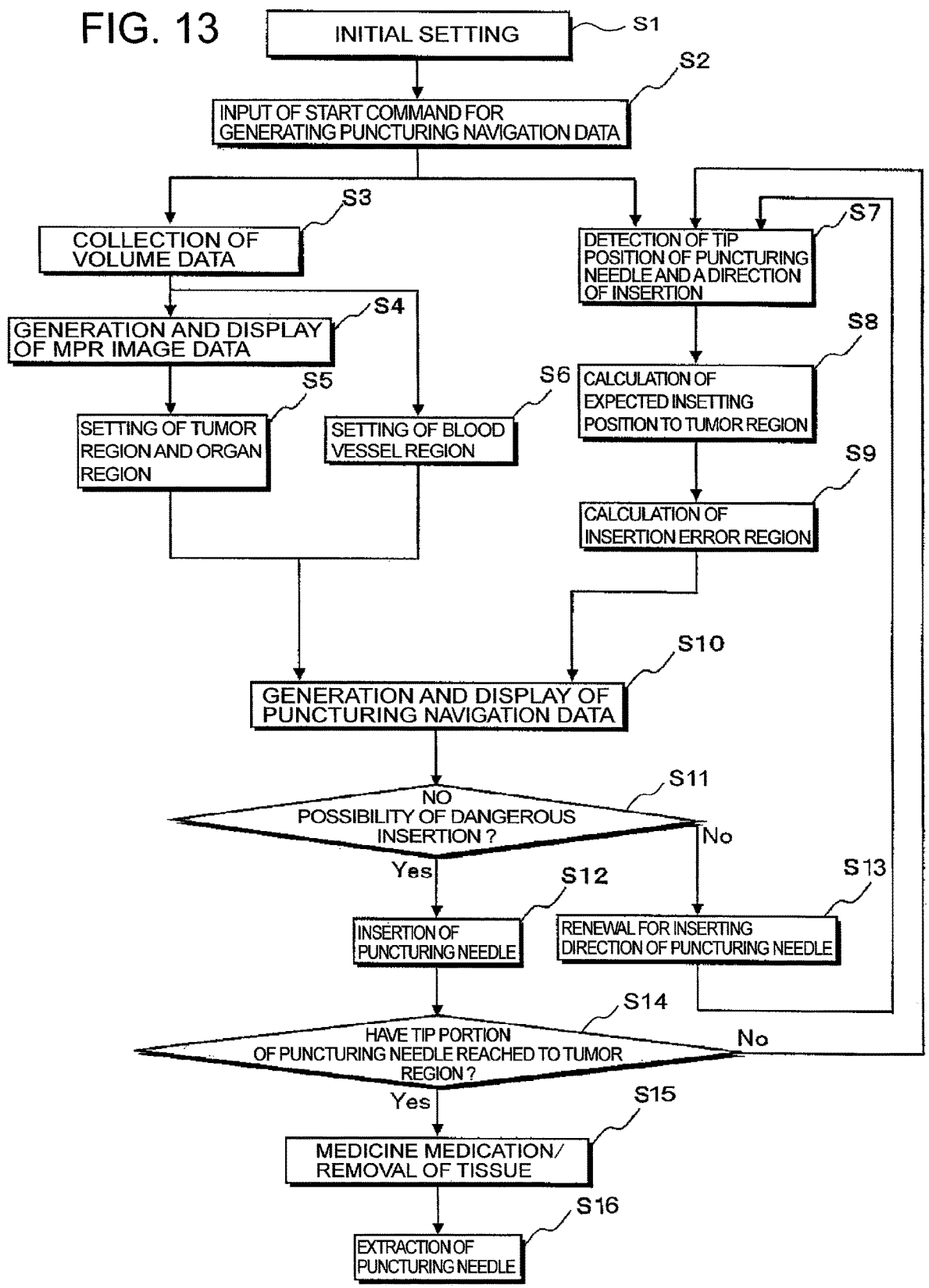
FIG. 13 is a flowchart illustrating a generating process of the puncturing navigation data in accordance with the embodiment of the ultrasound imaging diagnosis apparatus consistent with the present invention.
Figure 14A:
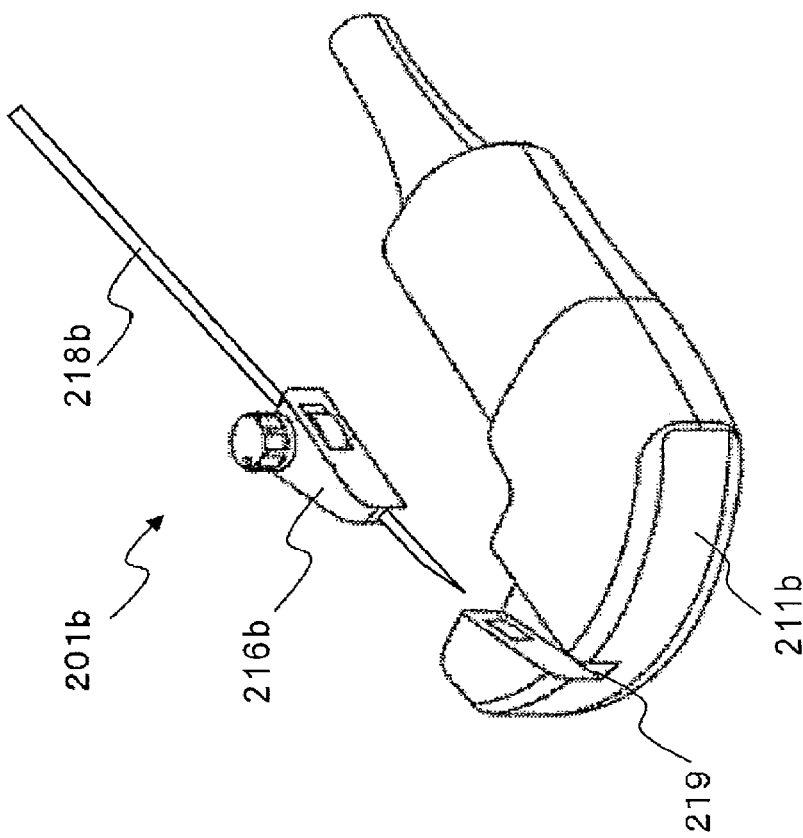
FIG. 14A illustrates one configuration of the conventionally proposed puncturing adaptor for an ultrasound probe.
Figure 14B:
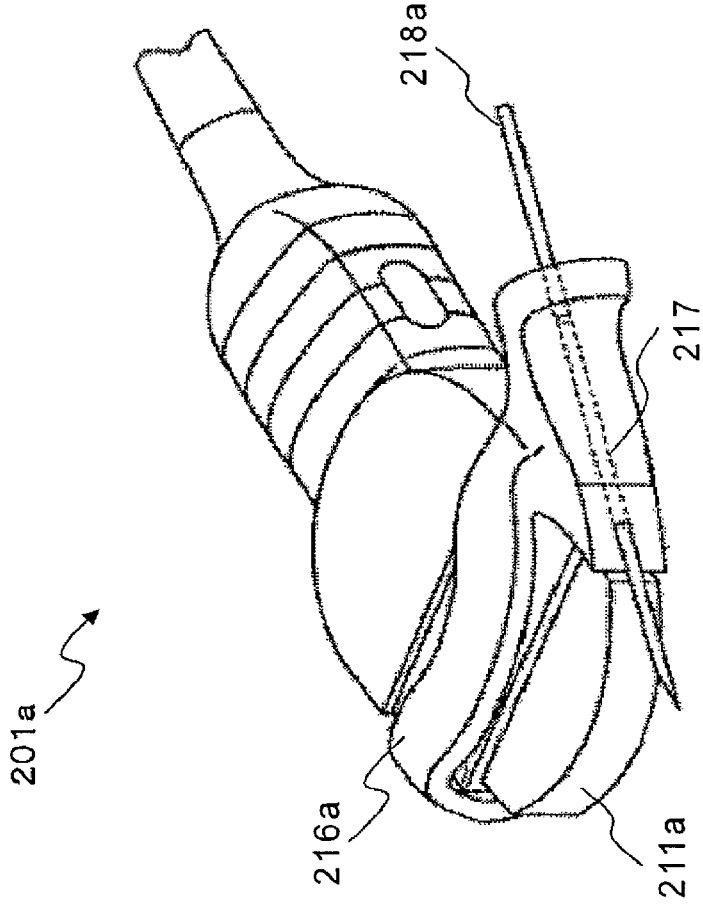
FIG. 14B illustrates another configuration of the conventionally proposed puncturing adaptor for an ultrasound probe.

FIG. 13 is a flowchart illustrating generation processes of the puncturing navigation data in accordance with the present embodiment of the invention. The operator for the ultrasound imaging diagnosis apparatus 100 initially inputs object data and a puncturing adaptor recognition data and also sets various conditions, such as, volume data acquisition conditions and display conditions of MPR image data, 3-D data or puncturing navigation data. Then the operator provides the ultrasound probe 3 on a desired position of the body surface of the object so as to set the puncturing needle 150 along the needle guide 161 of the puncturing adaptor 16 mounted on the ultrasound probe 3 (FIG. 13, step S1).

After completing the initial settings, the operator inputs start commands for generating the puncturing navigation data through the input unit 14 (FIG. 13, step S2). The generations of the puncturing navigation data are started by supplying the start command signals to the system control unit 15.

To acquire volume data for using generation of the puncturing navigation data, the rate pulse generator 211 in the transmission unit 21 (FIG. 2) generates rate pulses by dividing the reference signals supplied from the system control unit 15 in order to determine a recycle period for transmission ultrasound. The generated rate pulses are supplied to the transmission delay circuit 212. The transmission delay circuit 212 gives a convergence delay time for converging the transmission ultrasound into a prescribed depth and a deviation delay time for transmitting ultrasound in a plurality of transmission/reception directions ($\theta$p, $\varphi$q) to the rate pulses and supplies to the driving circuit 213. The driving circuit 213 generates driving signals based on the rate pulses supplied from the transmission delay circuit 212. The driving signals are supplied to the selected number N of transducers in the ultrasound probe 3 in order to emit transmitting ultrasounds into the body of an object.

As explained before in FIG. 2, the transmitted ultrasounds reflect at the boundary surfaces of the organs or tissues in the object and are received by the same transducers for the transmission as reception signals of N channels. The reception signals are amplified in the pre-amplifier 221 and are converted into digital signals in the A/D converter. Further, each of the reception signals are given a convergence delay time for converging reception ultrasound from a prescribed depth and a deviation delay time for setting a reception directivity to the first transmission/reception directions ($\theta$1, $\varphi$1). The reception signals acquired from the first transmission/reception direction ($\theta$1, $\varphi$1) are added in the adder 224.

The envelope detector 411 and the logarithmic converter 412 in the B mode data generating B mode data by detecting the envelope of the reception signals and performing logarithmic conversions. The generated B mode data are stored in the B mode data memory 51 in the volume data generating unit 5 with attaching transmission/reception directions as affixed data.

When the generation of the B mode data along the first transmission/reception direction ($\theta$1, $\varphi$1) has completed and stored them, the system control unit 15 controls the respective delay times of the transmission delay circuit 212 in the transmission unit 21 and the reception delay circuit 223 in the reception unit 22 so as to successively perform 3-D scans by transmitting and receiving ultrasound along the transmission/reception directions ($\theta$p, $\varphi$q) with successively renewing along the azimuth ($\theta$) direction by $\Delta\theta$ and along the elevation ($\varphi$) direction by $\Delta\varphi$ as illustrated in FIG. 2, i.e., $\theta p = \theta 1 + (p-1) \Delta\theta$ (2 to p), $\varphi q = \varphi 1 + (q-1) \Delta\varphi$ (q=2 to Q). The B-mode data acquired at each of the transmission/reception directions are stored in the B-mode data memory unit 51 (FIG. 4). The system control unit 15 further transmits and receives ultrasound in order to acquire color Doppler data in parallel to the acquisition of B-mode data along the directions ($\theta$p, $\varphi$q) (p=1~p, q=1~Q).)

The system control unit 15 further performs ultrasound transmission/reception for acquiring color Doppler data in the transmission/reception directions with substantially parallel to the ultrasound transmission/reception for acquiring B mode data to the above-described transmission/reception directions ($\theta$p, $\varphi$q), (p=1 to P, q=1 to Q). Thus, at first, the system control unit 15 repeats the ultrasound transmission/reception by a predetermined times (L times) along the transmission/reception directions ($\theta$1, $\varphi$1) by controlling the transmission delay times at the transmission delay time in the transmission unit 21 and the reception delay times at the reception delay circuit 212 in the reception delay circuit 223 in the reception unit 22 in order to supply the reception signals acquired from the reception unit 22 in each of the ultrasound transmission/reception to Doppler signal detection unit 42. In the Doppler signal detection unit 42, an orthogonally phase detection is carried out from the reception signals. The detected Doppler signals are stored in the Doppler signal memory circuit 431 in the color Doppler data generating unit 43.

When the storage of the Doppler signals acquired by performing the predetermined L times of the ultrasound transmission and reception in the first transmission/reception direction ($\theta$1, $\varphi$1) has completed, the system control unit 15 successively reads L numbers of Doppler signals corresponded to a prescribed position or depth among the Doppler signals stored in the Doppler signal memory circuit 431 and supplies to the MTI filter 432. The MTI filter 432 extracts Doppler components due to the blood flow by performing a filtering process of the supplied Doppler signals and supplies to the auto-correlation computing unit 433.

The auto-correlation computing unit 433 performs the auto-correlation calculation by using Doppler signals supplied from the MTI filter 432 and further calculates blood flow data based on the result of the auto-correlation calculation. The same calculations are performed at the different positions or the depths. The blood flow data in the calculated transmission/reception direction ($\theta$1, $\varphi$1) are stored in the color Doppler data memory unit 52 in the volume data generating unit 5 as an affixed data.

The system control unit 15 further performs 3-D scans by transmitting and receiving ultrasound in each of the transmission/reception directions ($\theta$p, $\varphi$q) ($\theta p = \theta 1 + (p-1)\Delta\theta$ (p=2 to P), $\varphi q = \varphi 1 + (q-1)\Delta\varphi$ (q=2 to Q). The acquired color Doppler data in each of the transmission/reception directions are stored in the color Doppler data memory unit 52 in the volume data generating unit 5 as affixed data.

The interpolation processing unit 53 in the volume data generating unit 5 generates 3-D B mode data by arranging the plurality of B mode data read out from the B mode data memory 51 as to correspond to each of the transmission/reception directions ($\theta$p, $\varphi$q), here, $\theta p = \theta 1 + (p-1) \Delta\theta$ (p=1 to P), $\varphi q = \varphi 1 + (q-1) \Delta\varphi$ (q=1 to Q). The interpolation processing unit 53 further generates B mode volume data by performing interpolation process for the 3-D B mode data. Similarly, the interpolation processing unit 53 generates 3-D color Doppler by arranging the plurality of color Doppler data read out from the color Doppler data memory 52 as to correspond to each of the transmission/reception directions and further generates color Doppler volume data by performing interpolation process for the 3-D color Doppler data. The generated B mode volume data and color Doppler volume data are stored in the volume data memory unit 54 (FIG. 13, step S3).

The MPR image data generating unit 6 reads out the B mode volume data stored in the volume data memory unit 54 in the volume data generating unit 5 in order to set a plurality of MPR planes that are crossing at a desired position on the tumor based on the MPR plane data supplied from the MPR plane setting unit 141 in the input unit 14. A plurality of MPR image data is generated by extracting voxels of the B mode volume data corresponded to these MPR planes. The generated MPR image data are displayed on the monitor in the display unit 12 (FIG. 13, step S4).

By observing the plurality of MPR image data displayed on the display unit 12, an operator sets each outlines of the tumor portion and other organs located near to the tumor portion based on each of the MPR image data by using the outline setting unit 142 in the input unit 14. By receiving the outline data of the tumor portion from the outline setting unit 142 through the system control unit 15, the tumor region setting unit 71 in the regions setting unit 7 sets 3-D tumor region designated by an approximate sphere body or a rotating elliptical body based on the outline data of the tumor portion. Similarly, the organ region setting unit 72 in the regions setting unit 7 sets 3-D organ regions designated by an approximate sphere body or a rotating elliptical body based on the outline data of the organs received by the outline setting unit 142 (FIG. 13, step S5).

The blood vessel region setting unit 73 reads the color Doppler volume data stored in the volume data memory unit 54 in the volume data generating unit 5 and sets the 3-D main blood vessels located surrounding the tumor portion as blood vessels regions based on the blood flow data of the color Doppler volume data (FIG. 13, step S6).

In parallel to the settings of the respective tumor region, organ region and blood vessel regions based on the above-mentioned volume data and MPR image data, the puncturing needle position detecting unit 9 detects the tip position and the inserting direction of the puncturing needle 150 at just before the insertion based on the slant angle data of the needle guide 161 supplied from the system control unit 15 (FIG. 13, step S7).

By receiving the tip position data and inserting direction data of the puncturing needle 150 at just before the insertion from the puncturing needle position detecting unit 9, the expected inserting position calculating unit 10 calculates a distance between the tip position of the puncturing needle 150 and the tumor region. The expected inserting position calculating unit 10 further calculates an expected inserting position to the tumor region by supporting that the puncturing needle 150 goes straight in the living body to the distance between the tip position of the puncturing needle and the tumor region (FIG. 13, step S8).

The expected inserting position calculating unit 10 further calculates an insertion error region of a possible error scope of the expected inserting position by assuming a bend degree during the insertion of the puncturing needle 150 based on various data of the distance between the tip position of the puncturing needle and the tumor region, material data of the puncturing needle 150 supplied from the system control unit 15 and the anatomy data of the living body (FIG. 13, step S9).

The puncturing navigation data generating unit 11 generates the puncturing navigation data just before the insertion based on the data supplied from the regions setting unit 7, i.e., tumor region data, blood vessel regions data and organ region data, the inserting direction data of the puncturing needle 150 supplied from the puncturing needle position detecting unit 9, the expected inserting position data to the tumor region and the insertion error region data that are supplied from the expected inserting position calculating unit 10. The generated puncturing navigation data are displayed on a monitor in the display unit 12 (FIG. 13, step S10).

In parallel to the generation of the puncturing navigation data, the 3-D data generating unit 8 generates 3-D data by composing the 3-D data of tumor region, organ region and blood vessel regions and the data of tip position and inserting direction of the puncturing needle 150 that are detected by the puncturing needle position detecting unit 9. The generated 3-D data are displayed on the display unit 12 as reference data for the puncturing navigation data depend on a necessity.

When it is confirmed that the expected inserting position and the insertion error region do not pile up nor contact to the organ region or the blood vessels regions in the puncturing navigation data by observing the puncturing navigation data displayed on the monitor in the display unit 12, thus, if no possibility of dangerous insertion is confirmed (FIG. 13, step S11, Yes), the operator starts the insertion of the puncturing needle 150 into the body of the object (FIG. 13, step S12). If the operator finds that the organ region or the blood vessel region in the puncturing navigation data pile up or contact to the expected inserting position or the insertion error region, the operator renews the position of the ultrasound probe 3, the inserting direction or inserting position of the puncturing needle 150 (FIG. 13, step S13). Then the above-mentioned steps S3-S11 are repeated.

When the puncturing needle 150 has inserted into the body of the object at the step S12, if the tip portion of the puncturing needle 150 has not yet reached to the tumor region (FIG. 13, step S14, No), the puncturing needle position detecting unit 9 (FIG. 1) detects the tip position of the puncturing needle 150 during the insertion based on the reception signals of ultrasound reflection data obtained through the tip portion. Further, the puncturing needle position detecting unit 9 detects the inserting direction of the puncturing needle 150 based on the time variation of the tip position (FIG. 13, step S7).

The tip position data and inserting direction data of the puncturing needle 150 during the insertion detected by the puncturing needle position detecting unit 9 are supplied to the expected inserting position calculating unit 10 (FIG. 1) in order to calculate the distance between the tip of the puncturing needle puncturing needle and the tumor region. The expected inserting position calculating unit 10 further calculates the expected inserting position and the insertion error region against the tumor region based on the material data of the puncturing needle 150 and the anatomy data of the living body that are supplied through the system control unit 15 (FIG. 13, steps S8 and S9).

The puncturing navigation data generating unit 11 (FIG. 1) generates the puncturing navigation data during the insertion based on various data, i.e., data of the tumor region, blood vessel regions and organ region that are supplied from the regions setting unit 7, the inserting direction data of the puncturing needle 150 during the insertion that are supplied from the puncturing needle position detecting unit 9 and the expected inserting position data and the insertion error region data that are supplied from the expected inserting position calculating unit 10. The generated puncturing navigation data is displayed on the monitor in the display unit 12 (FIG. 13, step S10).

The insertion of the puncturing needle 150 into the body is proceeded with monitoring the puncturing navigation data displayed on the monitor in the display unit 12 (FIG. 13, step S12). When the arrival of the tip portion of the puncturing needle 150 to the tumor region (FIG. 13, step S14, Yes), inspections or treatments, such as medicine medications or removal of tissue of the tumor, are executed with stopping the insertion of the puncturing needle 150 (FIG. 13, step S15). After completing some prescribed treatments, the puncturing needle 150 is extracted from the body of the object (FIG. 13, step S16).

According to the embodiment in consistent with the present invention, as explained above, the tumor region and the neighboring organ region are approximated as a sphere body or a rotation ellipse body and the main blood vessels region are indicated by the outlines. Thus, the puncturing navigation data is generated by composing these regions data. Consequently, it becomes possible to emphasize such a notable tumor portion, other organ or blood vessels during the treatments by using the puncturing needle in the monitor display. Thus, according to the ultrasound imaging diagnosis apparatus consistent with the present invention, it becomes possible to significantly improve the efficiency and the safeness of puncturing diagnostic examinations and treatments and can significantly reduce the burdens of the puncturing operators and injuring risks to the patient.

According to the embodiment in consistent with the present invention, it becomes possible to eliminate the organ region or the blood vessel regions that are located at the front portion of the tip portion of the puncturing needle in accordance with the insertion depth of the puncturing needle. Thus, the organ region or the blood vessel regions that locate at the dangerous insertion region only can be displayed as an emphasized puncturing navigation data.

According to the embodiment in consistent with the present invention, it becomes possible to easily confirm each of position relationship among the blood vessel regions or the organ region in the puncturing navigation data by displaying different colors or brightness in accordance with the distances from the body surface. Further, it becomes possible to easily recognize the tumor region, the organ region and the blood vessel regions by using different displaying colors or brightness.

According to the embodiment in consistent with the present invention, when the organ region or blood vessel regions in the puncturing navigation data are displayed by overlapping or contacting to the expected inserting position or the insertion error region, the warning signals are generated in order to re-setup the inserting position or the inserting direction of the puncturing needle. Consequently, it can perfectly prevent a dangerous insertion from occurring. Further, since the expected inserting position or the surrounded portion is displayed with blinking in the puncturing navigation data, it becomes possible to accurately confirm a timing that the tip portion of the puncturing needle reaches to the tumor. Consequently, it can prevent an excessive insertion into the tumor region from occurring.

According to the embodiment in consistent with the present invention, the puncturing navigation data is generated by composing the tumor region, organ region and blood vessel regions together with the expected inserting position and the insertion error region along the eye direction corresponded with the inserting direction of the puncturing needle. Consequently, it can easily and accurately know the position relationship between the puncturing needle and each of the tumor region, organ region and blood vessel regions.

According to the embodiment in consistent with the present invention, it becomes possible to significantly improve the efficiency and the safety of puncturing diagnostic examinations and treatments. It becomes also possible to significantly reduce the burdens of the puncturing operators and injuring risks to the patient. Particularly, not only the expected insertion region of the puncturing needle but the insertion error region also is set the tumor region in the puncturing navigation data with considering possible flexion of the puncturing needle during the insertion. This is significantly efficient to improve the safeness of ultrasound diagnostic examinations and treatments by using the puncturing needle.

The present invention does not limited to the above-mentioned embodiment. In the above-mentioned embodiment, the volume data are generated based on the 3-D B mode data and 3-D color Doppler data acquired through the 2-D array ultrasound probe in which a plurality of transducers are arranged in two directions. And the 3-D tumor region, 3-D organ region and 3-D blood vessel regions are approximately set as a sphere or an ellipse body by using the generated volume data. It is also possible to acquire the volume data by mechanically moving the 1-D array ultrasound probe. Moreover, it is possible to set the blood vessel region by using the volume data based on the B mode data at the time of contrast media medication instead of the usage of the color Doppler data.

In the above-mentioned embodiment, 3-D tumor region or 3-D other organ region are set as an approximated sphere or a rotation ellipse body based on the outline data that are manually set to the MPR image data. Of course, it is also possible to automatically set the tumor region or other organ region by performing binary conversion of the volume data.

As the puncturing needle applicable to the present invention, various types of catheter are included, such as an RFA (Radio Frequency Ablation) puncturing needle that can perform ablation for the inspection/treated areas, such as a tumor, and other catheters that can perform medicine medication or organization extraction to the inspection/treated area.

In the above-mentioned embodiment, an ultrasound diagnosis apparatus has explained. Of course, the puncturing navigation control system consistent with the present invention can be applicable to another type of the imaging diagnosis apparatus, such as a CT apparatus.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

What is claimed is:

1. An ultrasound apparatus comprising:
   scanned data acquiring circuitry configured to acquire acquired data from a scan region on an object;
   a puncturing needle position detector configured to detect a position of a puncturing needle inserted in a body of the object;
   processing circuitry configured to calculate an expected inserting position to a target region and an insertion error region based on the position of the puncturing needle, generate a puncturing navigation image by a rendering process or projection process of a three dimensional image of a target region set by using the acquired data along an inserting direction of the puncturing needle as an eye direction such that images of the expected inserting position and the insertion error region viewed from the inserting direction are superimposed on an image of a representation of the target region viewed from the inserting direction in the puncturing navigation image and such that the image of the expected inserting position is located at a center portion in a display area where the puncturing navigation data is displayed, wherein the image of the insertion error region is a circle image larger than the image of the expected inserting position and resized according to the position of the puncturing needle, and the image of the expected inserting position is within the image of the insertion error region; and a display including a screen and configured to display the puncturing navigation image on the display area of the screen of the display.

2. The ultrasound apparatus according to claim 1, wherein the processing circuitry is configured to perform, when generating the puncturing navigation image, the rendering process or the projection process of blood vessel regions data or organ region data along the inserting direction of the puncturing needle as the eye direction.

3. The ultrasound apparatus according to claim 1, a further comprising volume data acquiring is circuitry configured to acquire volume data, as the acquired data, from a volume (3-D) scan region on the object.

4. The ultrasound apparatus according to claim 3, further comprising region setting circuitry configured to generate the representation of the target region of the object from the volume data based on one or a plurality of MPR (multi-planar reconstruction) image data generated from the volume data.

5. The ultrasound apparatus according to claim 4, wherein the region setting circuit is further configured to set the 3-D region approximated by a sphere or a rotation ellipse as the representation of the target region.

6. The ultrasound apparatus according to claim 1, wherein the display is further configured to display the expected inserting position or a near position thereof with blinks when the expected inserting position of the puncturing needle reaches to the target region.

7. The ultrasound apparatus according to claim 1, wherein the processing circuitry is configured to gradually reduce a size of the image of the insertion error region in accordance with an increase of an insertion depth of the puncturing needle.

8. An imaging apparatus comprising:
scanned data acquiring circuitry configured to acquire data from a scan region on an object;
a puncturing needle position detector configured to detect a position of a puncturing needle inserted in a body of the object;
processing circuitry configured to
generate a puncturing navigation image by a rendering process or projection process of a three dimensional image of a target region set by usinu the acquired data along an inserting direction of the puncturing needle as an eye direction such that images of a needle position of the puncturing needle and an insertion error region viewed from the inserting direction are superimposed on an image of a representation of the target region viewed from the inserting direction in the puncturing navigation image and such that the image of the needle position is located at a center portion in a display area where the puncturing navigation data is displayed, wherein the image of the insertion error region is a circle image lamer than the image of the needle position and resized according to the needle position, and the image of the needle position is within the image of the insertion error region; and a display including a screen and configured to display the puncturing navigation image on the display area of the screen of the display.

9. A needling navigation controlling method for an imaging apparatus, the needling navigation controlling method comprising:
acquiring data from a scan region on an object;
detecting a position of a puncturing needle inserted in a body of the object;
generating a puncturing navigation image by a rendering a process or projection process of a three dimensional image of a target region included in set by using the acquired data along an inserting direction of the puncturing needle as an eye direction such that images of a needle position of the puncturing needle and an insertion error region viewed from the inserting direction are superimposed on an image of a representation of the target region viewed from the inserting direction in the puncturing navigation data and such that the image of the needle position is located at a center portion in a display area where the puncturing navigation data is displayed, wherein the image of the insertion error region is a circle image larger than the image of the needle position and resized according to the needle position, and the image of the needle position is within the image of the insertion error region: and displaying the puncturing navigation data on the display area of a screen.

\* \* \* \* \*